United States Patent
Nestor et al.

(10) Patent No.: US 10,925,509 B2
(45) Date of Patent: Feb. 23, 2021

(54) SYSTEM AND METHOD FOR GENERATING VISUAL IDENTITY AND CATEGORY RECONSTRUCTION FROM ELECTROENCEPHALOGRAPHY (EEG) SIGNALS

(71) Applicant: THE GOVERNING COUNCIL OF THE UNIVERSITY OF TORONTO, Toronto (CA)

(72) Inventors: Adrian Razvan Nestor, Toronto (CA); Dan Nemrodov, Thornhill (CA)

(73) Assignee: THE GOVERNING COUNCIL OF THE UNIVERSITY OF TORONTO, Toronto (CA)

(*) Notice: Subject to any disclaimer, the term of this patent is extended or adjusted under 35 U.S.C. 154(b) by 106 days.

(21) Appl. No.: 16/423,064

(22) Filed: May 27, 2019

(65) Prior Publication Data

US 2019/0357797 A1 Nov. 28, 2019

Related U.S. Application Data

(60) Provisional application No. 62/677,138, filed on May 28, 2018.

(51) Int. Cl.
*G06K 9/00* (2006.01)
*A61B 5/0484* (2006.01)
(Continued)

(52) U.S. Cl.
CPC ........ *A61B 5/04842* (2013.01); *A61B 5/0478* (2013.01); *A61B 5/6814* (2013.01);
(Continued)

(58) Field of Classification Search
None
See application file for complete search history.

(56) References Cited

U.S. PATENT DOCUMENTS

2006/0161218 A1* 7/2006 Danilov ................ A61B 5/486
607/45
2012/0059273 A1* 3/2012 Meggiolaro ......... A61B 5/7264
600/544
(Continued)

OTHER PUBLICATIONS

Ling, S, Lee, ACH, Armstrong, BC, Nestor, A. How are visual words represented? Insights from EEG-based visual word decoding, feature derivation and image reconstruction. Hum Brain Mapp. 2019; 40: 5056-5068. https://doi.org/10.1002/hbm.24757 (Year: 2019).*

(Continued)

*Primary Examiner* — Hadi Akhavannik
(74) *Attorney, Agent, or Firm* — Bhole IP Law; Anil Bhole; Marc Lampert

(57) ABSTRACT

There is provided a system and method for generating visual category reconstruction from electroencephalography (EEG) signals. The method includes: receiving scalp EEG signals; using a trained pattern classifier, determining pairwise discrimination of the EEG signals, the pattern classifier trained using a training set comprising EEG signals associated with a subject experiencing different known visual identities; determining discriminability estimates of the pairwise discrimination of the EEG signals by constructing a confusability matrix; generating a multidimensional visual representational space; determining visual features for each dimension of the visual representational space by determining weighted sums of image stimulus properties; identifying subspaces determined to be relevant for reconstruction; and reconstructing the visual appearance of a reconstruction target using estimated coordinates of the target and a summed linear combination of the visual features proportional with the coordinates of the target in the visual representational space.

20 Claims, 14 Drawing Sheets

(51) Int. Cl.
- *A61B 5/0478* (2006.01)
- *A61B 5/00* (2006.01)
- *G06K 9/62* (2006.01)
- *G06N 20/10* (2019.01)
- *G06N 7/00* (2006.01)

(52) U.S. Cl.
CPC ............ *A61B 5/7225* (2013.01); *G06K 9/628* (2013.01); *G06K 9/6269* (2013.01); *G06N 7/005* (2013.01); *G06N 20/10* (2019.01)

(56) References Cited

U.S. PATENT DOCUMENTS

| | | | | |
|---|---|---|---|---|
| 2013/0184558 A1* | 7/2013 | Gallant | ................ | A61B 5/0042 600/409 |
| 2014/0031952 A1* | 1/2014 | Harshbarger | ............ | A61F 2/54 623/25 |
| 2015/0297106 A1* | 10/2015 | Pasley | .................... | G10L 25/48 600/378 |
| 2018/0177619 A1* | 6/2018 | Zhang | .................... | G06N 3/061 |
| 2019/0247662 A1* | 8/2019 | Poltroak | ............ | A61B 5/04009 |

OTHER PUBLICATIONS

Andrews TJ, Baseler H, Jenkins R, Burton AM, Young AW. Contributions of feature shapes and surface cues to the recognition and neural representation of facial identity. Cortex. Oct. 2016;83:280-91. doi: 10.1016/j.cortex.2016.08.008. Epub Aug. 26, 2016. PMID: 27636006. (Year: 2016).*

Nemrodov, D., Niemeier, M., Patel, A., & Nestor, A. (2018). The neural dynamics of facial identity processing: Insights from EEG-based pattern analysis and image reconstruction. Eneuro, 5, Jan. 1, 2018.

Nemrodov, D., Behrmann, M., Niemeier, M., Drobotenko, N., & Nestor, A. (2019). Multimodal evidence on shape and surface information in individual face processing. NeuroImage, 184, (January), 813-825.

* cited by examiner

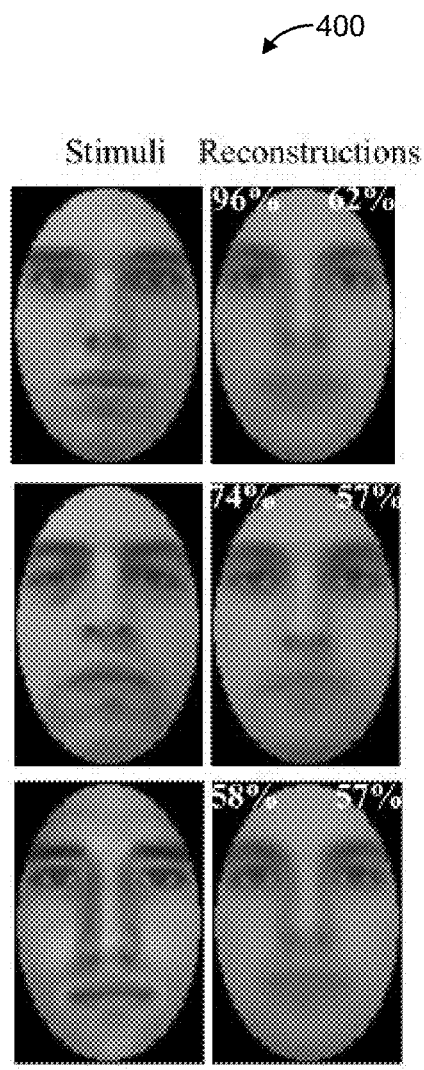
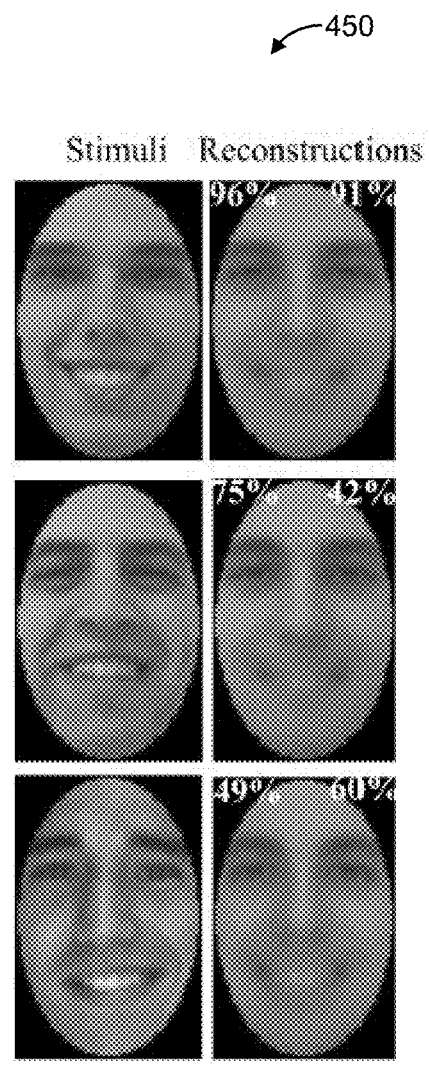
FIG. 4A
FIG. 4B

SYSTEM AND METHOD FOR GENERATING VISUAL IDENTITY AND CATEGORY RECONSTRUCTION FROM ELECTROENCEPHALOGRAPHY (EEG) SIGNALS

TECHNICAL FIELD

The following relates generally to neural-based image reconstruction; and more particularly, to systems and methods for converting electroencephalography (EEG) signals to identifiable images.

BACKGROUND OF THE INVENTION

Researchers have attempted various ways to reconstruct images that approximate the subjective mental content associated with experiencing visual stimuli using neuroimaging techniques. One way involves reconstructing such images from functional magnetic resonance imaging (fMRI) data using encoding models that predict brain responses from objective stimulus properties. Techniques using fMRI, which measures brain activity by detecting changes in blood flow, can generate fine details of activity in specific areas of the brain. The use of fMRI is generally uncommon, expensive, and/or unportable. Generally, fMRI also lacks temporal resolution; meaning fMRI generally cannot make detailed measurements of how a percept develops in time, for example at millisecond granularity.

SUMMARY OF THE INVENTION

In an aspect, there is provided a computer-implemented method for generating visual category reconstruction from electroencephalography (EEG) signals, the method comprising: receiving scalp EEG signals from one or more channels; using a trained pattern classifier, determining pairwise discrimination of the EEG signals, the pattern classifier trained using a training set comprising EEG signals associated with a subject experiencing different known visual identities; determining discriminability estimates of the pairwise discrimination of the EEG signals by constructing a confusability matrix; generating a multidimensional visual representational space; determining visual features for each dimension of the visual representational space by determining weighted sums of image stimulus properties; identifying subspaces determined to be relevant for reconstruction; reconstructing the visual appearance of a reconstruction target using estimated coordinates of the target and a summed linear combination of the visual features proportional with the coordinates of the target in the visual representational space; and outputting the reconstruction.

In a particular case of the method, the method further comprising separating the EEG signals into epochs by selecting recordings from a given temporal interval relative to a specific event.

In another case, the EEG signals from multiple epochs pertaining to the same specific event are averaged.

In yet another case, the pattern classifier comprises a linear Support Vector Machine.

In yet another case, the method further comprising determining classification accuracy for each pair of the pairwise discrimination by averaging across iterations.

In yet another case, generating the multidimensional visual representational space comprises estimating a fit between homologous spaces by aligning one space to the other and measuring the badness of fit as the sum of squared errors (SSE) between the two spaces.

In yet another case, identifying the subspaces comprises determining dimensions containing pixel values significantly different from chance.

In yet another case, the visual features are from human facial images, and wherein determining the visual features comprises: converting face stimuli to a CIEL*a*b* color space; summing the face stimuli proportionally to their normalized coordinates on a given dimension of face space; and determining the visual features as a linear approximation of the summed face stimuli along a specific dimension.

In yet another case, reconstructing the visual appearance of the reconstruction target comprises aligning at least one expressive face space to a neutral face space using Procrustes transformation, and projecting a remaining expressive face space into the neutral face space using parameters of a Procrustes mapping function.

In yet another case, the visual features are images of words, and wherein determining the visual features comprises: summing word stimuli proportionally to their normalized coordinates on a given dimension of visual word space; and determining the visual features as a linear approximation of the summed word stimuli along a specific dimension.

In yet another case, reconstructing the visual appearance of the reconstruction target comprises aligning at least an uppercase visual word space to a lowercase visual word space counterpart using Procrustes transformation, and projecting a remaining uppercase visual word space into the lowercase visual word space using parameters of a Procrustes mapping function.

In yet another case, the EEG signals are collected from twelve electrodes situated over homologue occipitotemporal areas.

In another aspect, there is provide a system for generating visual category reconstruction from scalp electroencephalography (EEG) signals, the system comprising one or more processors and a data storage device, the one or more processors configured to execute: an input module to receive the scalp EEG signals from one or more channels; a classification module to, using a trained pattern classifier, determine pairwise discrimination of the EEG signals, the pattern classifier trained using a training set comprising EEG signals associated with a subject experiencing different known visual identities; a reconstruction module to: determine discriminability estimates of the pairwise discrimination of the EEG signals by constructing a confusability matrix; generate a multidimensional visual representational space; determine visual features for each dimension of the visual representational space by determining weighted sums of image stimulus properties; identify subspaces determined to be relevant for reconstruction; and reconstruct the visual appearance of a reconstruction target using estimated coordinates of the target and a summed linear combination of the visual features proportional with the coordinates of the target in the visual representational space; and a display module to output the reconstruction.

In a particular case of the system, the pattern classifier comprises a linear Support Vector Machine.

In another case, generating the multidimensional visual representational space comprises estimating a fit between homologous spaces by aligning one space to the other and measuring the badness of fit as the sum of squared errors (SSE) between the two spaces.

In yet another case, identifying the subspaces comprises determining dimensions containing pixel values significantly different from chance.

In yet another case, the visual features are from human facial images, and wherein determining the visual features comprises: converting face stimuli to a CIEL*a*b* color space; summing the face stimuli proportionally to their normalized coordinates on a given dimension of face space; and determining the visual features as a linear approximation of the summed face stimuli along a specific dimension.

In yet another case, reconstructing the visual appearance of the reconstruction target comprises aligning at least one expressive face space to a neutral face space using Procrustes transformation, and projecting a remaining expressive face space into the neutral face space using parameters of a Procrustes mapping function.

In yet another case, the visual features are images of words, and wherein determining the visual features comprises: summing a word stimuli proportionally to its normalized coordinates on a given dimension of visual word space; and determining the visual features as a linear approximation of the summed word stimuli along a specific dimension.

In yet another case, reconstructing the visual appearance of the reconstruction target comprises aligning at least capital letter visual word space to a lowercase visual word space counterpart using Procrustes transformation, and projecting a remaining capital letter visual word space into the lowercase visual word space using parameters of a Procrustes mapping function.

These and other aspects are contemplated and described herein. It will be appreciated that the foregoing summary sets out representative aspects of the system and method to assist skilled readers in understanding the following detailed description.

BRIEF DESCRIPTION OF THE DRAWINGS

A greater understanding of the embodiments will be had with reference to the figures, in which:

FIGS. 4A and 4B illustrate reconstructions of facial images with neutral and happy expressions, along with estimates of their accuracy;

DETAILED DESCRIPTION

Figure 1:
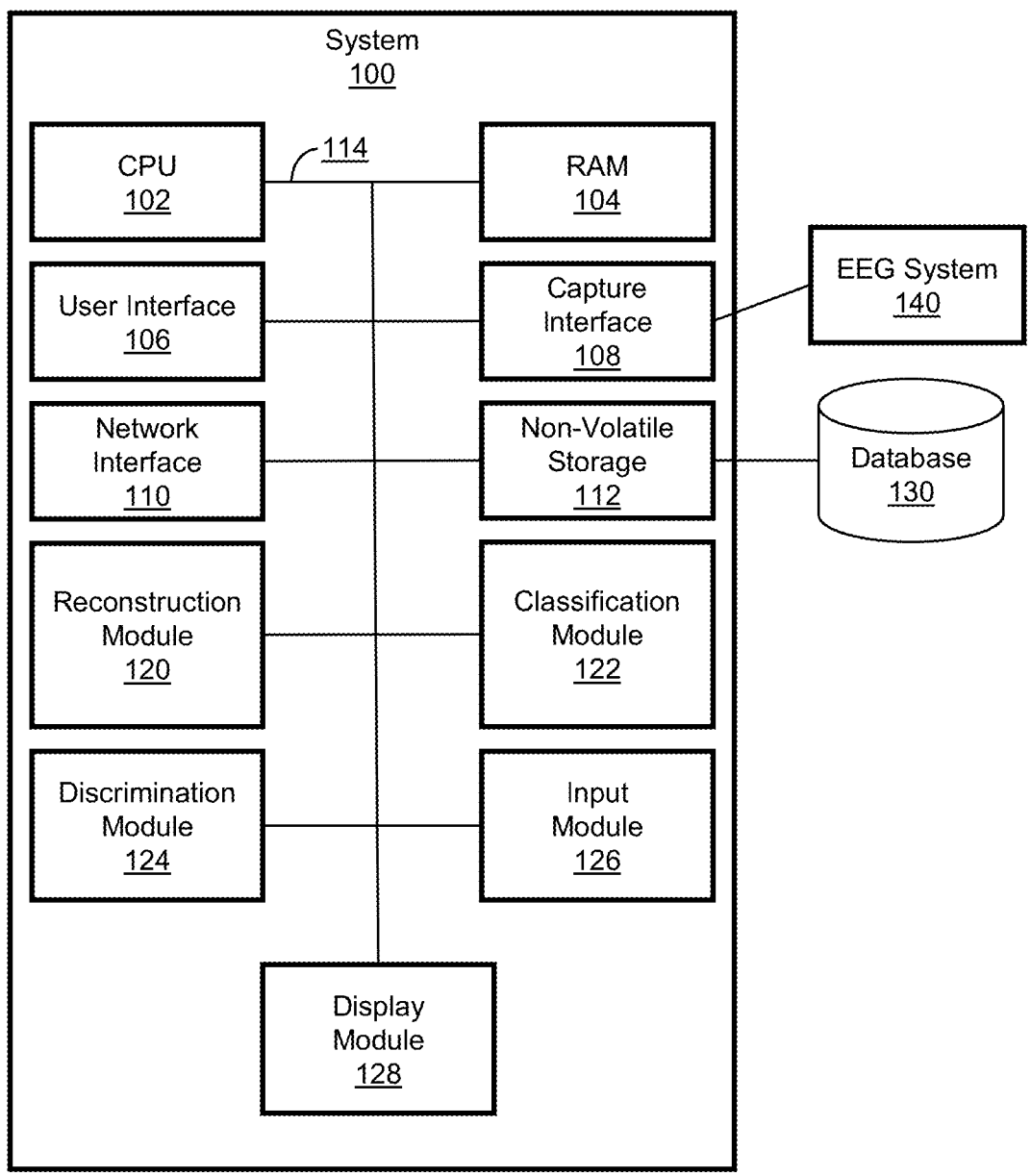
FIG. 1 illustrates a block diagram of a system for image reconstruction, according to an embodiment.

Embodiments will now be described with reference to the figures. For simplicity and clarity of illustration, where considered appropriate, reference numerals may be repeated among the Figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures, and components have not been described in detail so as not to obscure the embodiments described herein. Also, the description is not to be considered as limiting the scope of the embodiments described herein.

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender; "exemplary" should be understood as "illustrative" or "exemplifying" and not necessarily as "preferred" over other embodiments. Further definitions for terms may be set out herein; these may apply to prior and subsequent instances of those terms, as will be understood from a reading of the present description.

Any module, unit, component, server, computer, terminal, engine, or device exemplified herein that executes instructions may include or otherwise have access to computer-readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer-readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information, and which can be accessed by an application, module, or both. Any such computer storage media may be part of the device or accessible or connectable thereto. Further, unless the context clearly indicates otherwise, any processor or controller set out herein may be implemented as a singular processor or as a plurality of processors. The plurality of processors may be arrayed or distributed, and any processing function referred to herein may be carried out by one or by a plurality of processors, even though a single processor may be exemplified. Any method, application, or module herein described may be implemented using computer readable/executable instructions that may be stored or otherwise held by such computer-readable media and executed by the one or more processors.

Generally, scalp electroencephalography (EEG) data can be used for image reconstruction and is relatively inexpensive and portable. Advantageously, using embodiments described herein, the present inventors have developed technical approaches for overcoming some of the drawbacks of using scalp EEG signals; for example, such drawbacks may include (1) EEG signals giving insufficient information and containing artifacts; and (2) localization issues arising from the scalp acting like a diffuser.

Further, the use of explicit encoding models are generally constrained by assumptions regarding the nature of the function responsible for mapping stimulus properties onto brain responses and by the need to fit its parameters. Hence, approaches of the present embodiments that obviate the need for such models are advantageous because, for example, they avoid incorrect assumptions by reducing the complexity and increasing the efficiency of neural-based image reconstruction.

Neural-based image reconstruction of mental content from scalp electroencephalography (EEG) signals, as described herein, can be used in a number of applications. For example, applications that: (a) assess and/or confirm visual-cognitive functions indicative of awareness-consciousness in patients diagnosed with locked-in syndrome; (b) facilitate diagnosis for a range of neurodevelopmental disorders (e.g., autism spectrum disorder), learning disabilities (e.g., reading disorders), and personality or mood disorders (e.g., borderline personality disorder) typically associated with visual disturbances; (c) enhance face recognition performance in dedicated personnel (e.g., law enforcement); (d) augment eyewitness testimony (e.g., neural-based reconstructions of facial appearance from the memory of an eyewitness); (e) facilitate neural-based communication via brain-computer interfaces (e.g., reconstructions of visual word imagery), and the like.

Elucidating the dynamics of visual processing can allow for an understanding of its underlying mechanisms. To this end, characterizing a time course of visual processing can be determined through the use of electroencephalography (EEG) and magnetoencephalography (MEG) given the temporal resolution of these methods. Accordingly, the neural profile of face processing as reflected by spatiotemporal EEG patterns (i.e., across electrodes and time) can be determined. Comparatively less is generally known about the visual representations underlying the dynamics of neural processing, especially as related to stimulus identity; for example, a specific facial identity as opposed to human face as a general category. To overcome this lack of knowledge, one approach is to employ an image-reconstruction paradigm seeking to approximate the visual appearance of individual stimuli from spatiotemporal EEG patterns. Generally, this approach can determine whether the visual information involved in stimulus identification can be recovered from EEG signals and, further, whether such information can support the characterization of neural-based representational space along with the reconstruction of individual face images.

Some applications of pattern analysis focus on a temporal profile of stimulus discrimination at a category and an exemplar (i.e., identity) level. For instance, facial identity discrimination can be carried out using MEG and EEG. Results of these approaches have found multiple, distinct temporal windows sensitive to facial information and, consistent with results from monkey neurophysiology and human psychophysics, have estimated an early onset for such sensitivity. Further, the cortical source of this information is attributed primarily to the fusiform gyrus (FG) in line with homologous investigations of face identification using functional magnetic resonance imaging (fMRI).

Yet, the representational basis of stimulus identity that allows successful discrimination from neural data is not elucidated in the above approaches. For example, neural patterns elicited by face perception generally speak to the properties of a representational face space, or, more generally, of a representational similarity space. In an effort to clarify the nature of such representations, using fMRI, the study of representational spaces and neural-based image reconstruction has been combined. Specifically, this approach has derived visual features from the structure of FG-based space and, then, used such features for image reconstruction. However, this approach generally does not consider the temporal aspects of visual processing. This approach also generally does not assess the invariant structure of a representational space. For instance, face space invariance over common image transformations (for example, expression, lighting, or the like) is generally not explicitly investigated; and thus, it is not clear whether visual information critical for identification has been recovered through reconstruction.

In view of the above, the present inventors experimented with an exemplary approach, embodied in the embodiments described herein, that aimed to derive representational space constructs from the EEG signal associated with consecutive time windows separately for different stimuli; for example, individual faces with different emotional expressions (for example, neutral and happy) or individual words presented in different manners (for example, different font or letter case). In this exemplary approach, an appearance of one set of faces (e.g., happy) were reconstructed based on a structure of a representational space derived for other faces (e.g., neutral). This experiment provided exemplary evidence that the spatiotemporal information of EEG patterns, as described herein, is rich enough to support: (i) identity-level face discrimination; (ii) neural-based face space estimation; (iii) visual feature synthesis, and (iv) facial image reconstruction. Further, this approach can characterize the neural dynamics of expression-invariant face processing while, more generally, providing for the ability to perform EEG-based image reconstruction. Discussion of this approach is described in more detail herein.

The following embodiments generally provide technological solutions to the technical problems related to image reconstruction from EEG signals; for example, facial image reconstruction or visual word reconstruction. In view of these technical problems, the embodiments described herein provide, at least, determination of discriminability estimates based on classification of EEG patterns, estimation of multidimensional representational spaces from the structure of EEG data, derivation and selection of relevant visual features from the structure of representational spaces.

In the present embodiments, there is provided a system and method for converting EEG signals into approximations of visual mental content as experienced by human viewers. In this sense, approximations of mental content, in the form of identifiable face and word images, are constructed from EEG signals recorded at the scalp of individuals engaged in viewing, remembering, or imagining individual faces and words. In an embodiment, as described herein, the system can acquire and process EEG data, then combine derived image features into approximations of mental content.

In an aspect, embodiments construct images from EEG signals. Scalp EEG signals can be recorded from a number of channels (e.g., 12-64 channels) with the use of an EEG system (for example, Biosemi ActiveTwo, Biosemi B. V.) in individuals viewing or remembering a variety of images. EEG recordings are analyzed and characterized using, for example, signal processing and pattern classification techniques. Visual features can be derived from the structure of analyzed EEG recordings. Such features are combined into approximations of visual impressions (i.e., percepts or memories) associated with viewing or remembering, for example, individual images of faces and words.

One such embodiment is a method of constructing images from EEG signals accomplished by performing certain actions based on the above. These actions can include: recording EEG signals from channels with the use of an EEG system; analyzing and characterizing EEG recordings; deriving image features from the structure of the analyzed EEG recordings; and combining image features into approximations of visual impressions associated with viewing images. This method has been experimentally demonstrated by the present inventors to produce recognizable reconstructions of face images (above a statistically based chance level) in individuals who have undergone testing, as well as recognizable word images in an additional group of individuals.

Turning to FIG. 1, a system for reconstructing images from EEG signals 100 is shown, according to an embodiment. In this embodiment, the system 100 is run on a client-side device (for example, a smartphone or tablet). In further embodiments, the system 100 can be run on any other computing device; for example, a desktop computer, a laptop computer, a server, a smartwatch, or the like.

In some embodiments, the components of the system 100 are stored by and executed on a single computing system. In other embodiments, the components of the system 100 are distributed among two or more computer systems that may be locally or remotely distributed.

FIG. 1 shows various physical and logical components of an embodiment of the system 100. As shown, the system 100 has a number of physical and logical components, including a central processing unit ("CPU") 102 (comprising one or more processors), random access memory ("RAM") 104, a user interface 106, a capture interface 108, a network interface 110, non-volatile storage 112, and a local bus 114 enabling CPU 102 to communicate with the other components. CPU 102 executes an operating system, and various modules, as described below in greater detail. RAM 104 provides relatively responsive volatile storage to CPU 102. The user interface 106 enables an administrator or user to provide input via an input device, for example a mouse or a touchscreen. The user interface 106 can also output information to output devices, such as a display or speakers. In some cases, the user interface 106 can have the input device and the output device be the same device (for example, via a touchscreen). The capture interface 108 communicates with an EEG system 140 to capture one or more EEG signals. The EEG system 140 can comprise, for example, electrodes, a brain wave receptor, or the like. In further embodiments, the system 100 can retrieve already captured EEG signals directly from a database 130 that is locally stored or remotely from a database 130 via the network interface 110. EEG signals, as used herein, are understood to mean signals from the brain. The contents of such EEG signals are described in greater detail herein.

The network interface 110 permits communication with other systems, such as other computing devices and servers remotely located from the system 100, such as for a typical cloud-based access model. Non-volatile storage 112 stores the operating system and programs, including computer-executable instructions for implementing the operating system and modules, as well as any data used by these services. Additional stored data, as described below, can be stored in a database 130. During operation of the system 100, the operating system, the modules, and the related data may be retrieved from the non-volatile storage 112 and placed in RAM 104 to facilitate execution. In an embodiment, the system 100 further includes a number of modules to be executed on the one or more processors 102, including a reconstruction module 120, a classification module 122, a discrimination module 124, an input module 126, and a display module 128.

Figure 2:
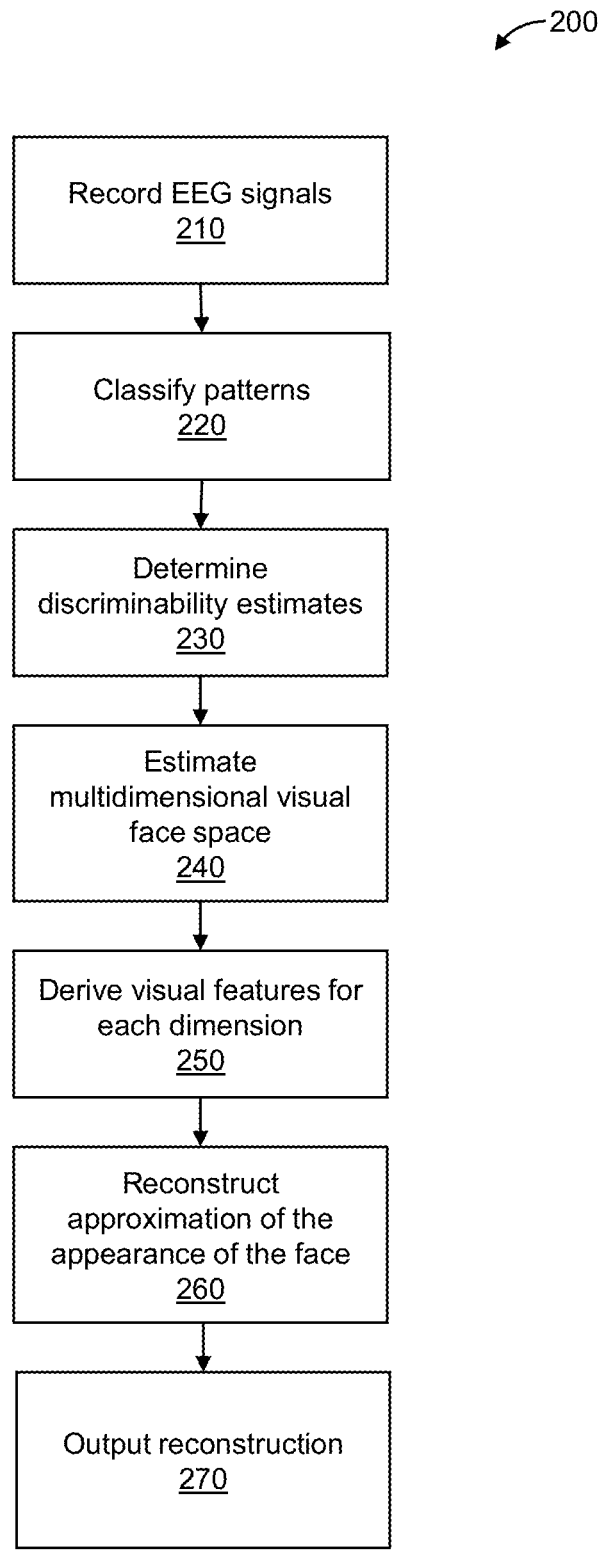
FIG. 2 illustrates a flow diagram of a method for facial image reconstruction, according to an embodiment.

FIG. 2 illustrates a method for facial image reconstruction 200, in accordance with an embodiment. In this embodiment of the system 100, as part of the method 200, the system 100 can reconstruct a facial image from EEG signals.

At block 210, the input module 126 receives and records EEG signals from the EEG system 140 via the capture interface 108 across multiple electrodes for each face. In an example, the input module 126 may record EEG data received from a 64-electrode Biosemi ActiveTwo EEG recording system. In this example, the electrodes can be arranged according to the International 10/20 System and the electrode offset can be kept below 40 mV. In some cases, the EEG system 140 or the input module 126 can apply a low-pass filter to the EEG data; for example, using a fifth order sinc filter with a half-power cutoff at 204.8 Hz. In some cases, the EEG system 140 or the input module 126 can digitize the EEG data, for example, at 512 Hz with 24 bits of resolution. In some cases, the EEG system 140 or the input module 126 can digitally filter the EEG data; for example, offline using a zero-phase 24 dB/octave Butterworth filter with a bandpass of 0.1-40 Hz.

In some cases, EEG data can be separated into epochs by the input module 126 by selecting recordings from a given temporal interval relative to a specific event; for example, stimulus presentation, forced eye blink, or the like. In an example, it can be divided into epochs from 100 ms prior to stimulus presentation or forced eye blink until 900 ms later, and in some cases, can be baseline-corrected. In some cases, epochs containing artifacts can be discarded. In further cases, noisy electrodes can be interpolated if necessary (for example, where it is desired to have no more than 2 such electrodes per subject) and epochs can be re-referenced to the average reference. In some cases, EEG data can be further cleaned of ocular artifacts; for example, using Infomax independent component analysis (ICA).

In an exemplary setup, twelve electrodes situated over homologue occipitotemporal areas (P5, P7, P9, PO3, PO7, O1 on the left and P6, P8, P10, PO4, PO8, O2 on the right) may be selected for ERP analysis. Their selection can be motivated by the relevance of these electrodes for face processing as revealed by ERP analysis (e.g., robust N170 amplitudes) as well as by their ability to maximize classification and/or reconstruction results following feature selection.

At block 220, the classification module 122 classifies patterns across the corresponding EEG signals. In some cases, in order to classify the patterns, epochs may be, for example, linearly detrended, z-scored across time and electrodes, and corrected for outliers (for example, values exceeding three standard deviations from the mean thresholded at ±3 to minimize the deleterious effect of extreme values on pattern classification). In some cases, the epochs may be normalized to the same range (for example, 0-1) and mean (for example, 0.5). In some cases, in order to boost signal-to-noise ratio (SNR) of spatiotemporal patterns, multiple epochs pertaining to a same condition (i.e., same viewed stimulus or same recalled image) may be averaged into ERP traces. In a particular case, all epochs corresponding to the same image stimulus, for a maximum of 4 epochs, may be averaged together resulting in 16 separate traces per stimulus. Advantageously, this approach can also be useful for handling missing data following epoch removal and in balancing the number of observations for pattern classification. Specifically, since it is possible that epochs associated with a given stimulus be removed (e.g., due to artifacts), in some cases this can lead to different numbers of epochs for different stimuli. However, in some cases, averaging data across consecutive epochs (i.e., 1-4 epochs per stimulus following data removal) may ensure that equal numbers of observations can be constructed for each pair of stimuli undergoing pattern classification.

In some cases, to increase the temporal resolution of pattern analyses and reconstruction (for example, when reconstructing video sequences, frame by frame, rather than a single stimulus image), epochs may be divided into temporal windows containing multiple bins; for example, 5 consecutive bins (5 bins*1.95 ms≈10 ms). Each window being a length of the temporal interval over which recordings are used for classification and/or reconstruction purposes (for example, a 10 ms window). For each window, data may be concatenated into observations; for example, data across selected occipitotemporal electrodes can be concatenated into 60-dimension observations (5 time bins× 12 electrodes). These observations can be constructed for the purpose of pattern analyses in time, window by window. In addition, more inclusive observations can be constructed that contain all time bins between 50 ms and 650 ms after stimulus presentation (3684-dimension vectors: 307 bins×12 electrodes), and, thus, both early and late information relevant for visual processing. These higher-dimensional observations can be constructed for the purpose of temporally cumulative analyses being able to exploit more extensive information over time, in some cases, at the cost of reduced temporal resolution, in these cases, they may be better suited for still image rather than video reconstruction.

In an embodiment, the classification module 122 can perform the classification using pairwise discrimination of stimulus identity or category (for example, pairs of face images displaying different individuals). In some cases, the discrimination module 124 can use linear Support Vector Machine (SVM) classification (c=1) and leave-one-out cross-validation (e.g., one out of 16 pairs of observations can be systematically left out for testing while the remaining 15 are used for training). In an example, the SVM can be trained using EEG-based observations, for example, corresponding to 1485 pairs of stimuli (i.e., each possible pair out of 55 stimuli). In some cases, the data can be validated, for example, using a leave-one-out cross-validation approach. In this case, classification accuracy can be obtained for each pair by averaging across the iterations. For example, in some cases, classification can be conducted for each pair of facial identities in two ways: (a) within expression, the classifier is trained separately on one expression (for example, happy or neutral) and tested on the same expression; and (b) across expression, the classifier is trained on one expression and tested on the other. Significance of classification accuracy can be assessed, for example, via a permutation test, by randomly shuffling identity labels (for example, for individual 1) a sufficient number of times (for example, $10^3$ times). While the present embodiment describes using an SVM, it is understood that any suitable machine learning technique or approach can be used; for example, other classification methods based on linear discrimination analysis or neural networks.

In some cases, classification may be conducted for data averaged across all or multiple participants (i.e., observations constructed from averaged ERP traces). In further cases, classification can be performed for data from individual participants. In some cases, the significance of the overall classification accuracy can be assessed using, for example, one-sample two-tailed t-tests against chance across participants.

At block 230, the reconstruction module 120 determines face discriminability estimates using a confusability matrix. In a particular case, classification accuracies for each pair of stimulus identities, as determined by pattern classification, can be organized into a confusability matrix in which each cell estimates the discriminability of a pair of faces. Thus, the matrix can contain information regarding the similarity and/or dissimilarity of any pair of stimulus identities. In some cases, the values of the cells can be further linearly scaled, for example, between 0 and 1.

In some cases, the reconstruction module 120 can derive representational space constructs; for example, multidimensional spaces in which different neural representations correspond to different points and their pairwise similarity is approximated as their space-dependent distance. For example, metric multidimensional scaling (MDS) can be applied to a confusability matrix to approximate a corresponding space. In an example, the dimensionality of such spaces can be restricted to 20, which may be sufficient to account for most variance in the data (for example, over 90%). This procedure can be conducted on within category estimates of discrimination; for example, within-expression for faces or within-font for words. For example, the face reconstruction procedure can be conducted separately for each expression, resulting in separate spaces for faces with neutral and happy expressions.

At block 240, the reconstruction module 120 determines a multidimensional visual face space from the structure of the data; i.e., a representational space dedicated to the encoding of facial identity. Face space invariance to image changes introduced by emotional expression can be determined. In most cases, the extent to which the structure of the space is sensitive to stimulus identity independently of other sources of image variability can be quantified and assessed by the reconstruction module 120. To this end, the fit between homologous spaces (for example, neutral and happy faces) can be estimated by aligning one space to the other, for example via Procrustes transformation, and measuring the badness of fit as the sum of squared errors (SSE) between the two spaces. This estimate can serve to confirm the presence of invariance and assess its robustness. For example, if a significant proportion of space structure is preserved despite image changes, the SSE fit should be better than expected by chance. Significance testing can be conducted, for example, through a permutation test for multidimensional spaces: the labels of each point in one of the two homologous spaces can be randomly shuffled and the resulting space fit to the intact one as above. In an example, this procedure can be carried out for a total of $10^3$ permutations, by leaving intact each of the two spaces half of the time while permuting the other space, and permutation-based SSE estimates can be determined each time. In some cases, image-invariant information, quantified and identified in this manner, can be used to constrain future reconstructions (i.e., as a prior) irrespective of image variability (e.g., due to expression or lighting).

In further embodiments of the system 100, different types of information, such as shape and surface information in the case of faces, can be considered separately in the reconstruction process. Since shape and surface often provide complementary cues to visual processing, separate types of CIMs can be derived corresponding to this distinction and assessed with respect to their separate contribution to image reconstruction; i.e., by separately reconstructing the shape and the surface properties of a target and then integrating the two into a joint reconstruction. Accordingly, shape and surface can be extracted from any given facial image using an active appearance model (AAM) approach that separates facial information into a geometric configuration of 2D or 3D fiducial points and a 'shape-free' surface map containing colour and texture information. Shape and surface descriptors can then be analyzed separately and, upon their independent reconstruction, re-combined via their AAM synthesis into image reconstruction.

At block 250, the reconstruction module 120 determines visual features for each dimension. Advantageously, the reconstruction module 120 can capitalize on the structure of neural-based representational space for the purpose of feature derivation and image reconstruction. For example, the reconstruction module 120 can capture spatiotemporal information in EEG patterns and determine the ability of invariant visual information to support image reconstructions of facial identity. In a particular case, the reconstruction module 120 can conduct this determination as follows: initially derive visual features for each dimension of EEG-based representational space; identify subspaces relevant for reconstruction purposes; and estimate the coordinates of a reconstruction target.

Figure 10A:
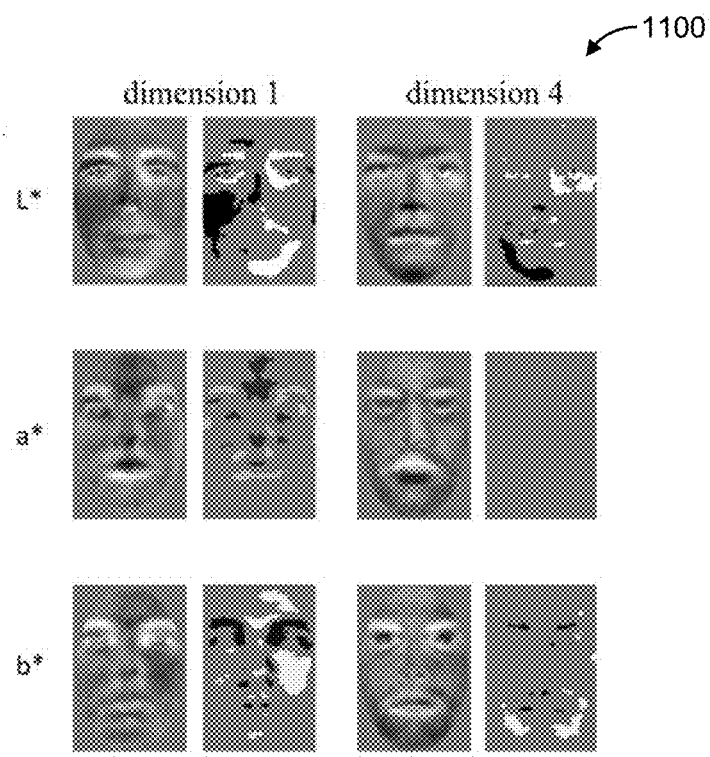
FIGS. 10A and 10B provide examples of classification images (CIMs) extracted from EEG-based face space constructs for neutral and happy faces.
Figure 10B:
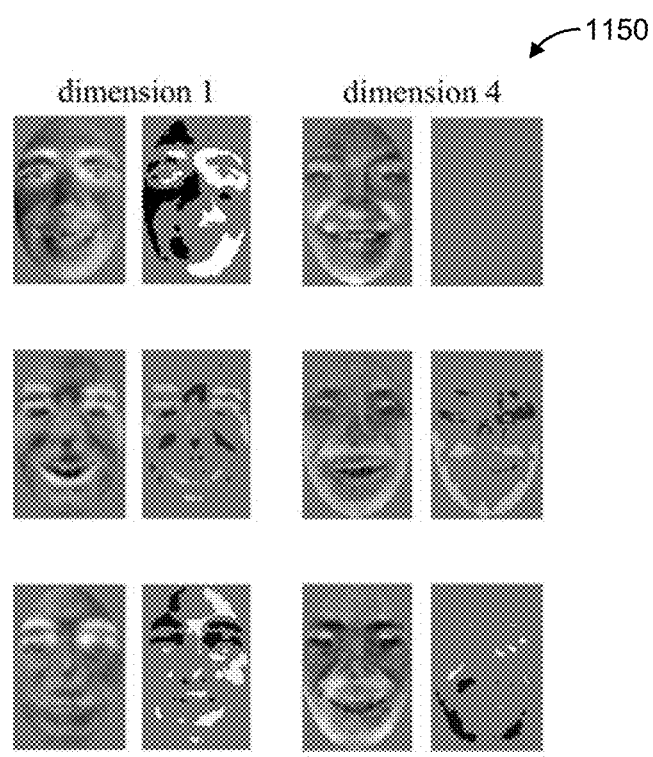

The reconstruction module 120 may separately derive visual features accounting for face space topography for each dimension of EEG-based face space; see FIGS. 10A and 10B for examples of such features. These features can be computed as weighted sums of stimulus properties, using for example, reverse correlation and/or image classification. Hence, here they can be referred to as 'classification images' (CIM). Face stimuli, for example following their color conversion to CIEL*a*b* color space, can be summed proportionally to their normalized (for example, z-scored) coordinates on a given dimension of face space. The resulting CIM (i.e., a triplet of images for the L*, a* and b* image components, roughly corresponding to the three color channels of human vision) would generally amount to a linear approximation of the visual information responsible for organizing faces along that specific dimension. For each expression, a total of, in this example, 20 different CIMs, one for each corresponding dimension of face space, can be determined.

In some cases, the reconstruction module 120 can identify subspaces relevant for reconstruction purposes using feature and/or dimension selection, since not all dimensions may encode systematic visual information. To this end, CIMs corresponding to each dimension can be assessed regarding the inclusion of significant information; information not due simply to noise. Specifically, for each dimension, permutation-based CIMs can be generated after randomly shuffling the coefficients associated with stimulus images; i.e., the coordinates of the stimuli in a given representational space. Pixel intensities in the true CIM can be compared to the corresponding intensities of pixels in permutation-based CIMs, for example for $10^3$ permutations. In this way, multiple comparison correction can be performed across pixels and/or color channels, for example using FDR, and only CIMs that contained pixel values significantly different from chance can be considered for reconstruction purposes.

In some cases, the reconstruction module 120 can estimate the coordinates of a target face in an expression-specific face space. The estimation of the representational space and its CIMs can be carried out, for example, using all but one of the target identities. The remaining identity can be projected in this space based on its similarity with the other items. Advantageously, this approach can be used to ensure that features are not generated from the reconstruction target, thus guarding against circularity; i.e., the reconstruction target is not reconstructed from features derived from its own image.

At block 260, the reconstruction module 120 reconstructs an approximation of the appearance of each face (referred to as a "target face") through the combination of the visual features. The reconstruction module 120 can construct the target face through a linear combination of significant CIMs. Relevant CIMs, as identified through feature selection above, can be multiplied by the target's coordinates in the representational space for the dimension corresponding to each CIM. CIMs can be normalized under specific constraints (e.g., proportional to the percentage of variance explained by each corresponding dimension) and summed together. This sum can be added to an average face obtained from all remaining non-target items and playing the role of a prior. The resulting image can be further normalized (e.g., with a set luminance average and contrast in case this is already known or derived independently from the data). Advantageously, the current procedure can capitalize on face space invariance for reconstruction purposes. For example, in the case of facial image reconstruction, a happy version of face space can be aligned to its neutral counterpart via, for example, Procrustes transformation using all but one face. The remaining face from the happy version of face space can be projected into the neutral space using, for example, the parameters of the Procrustes mapping function. In this case, the resulting coordinates in neutral face space can be used to reconstruct the appearance of the target face, with a neutral expression, from neutral CIMs. In further cases, a happy version of the target face can rely on aligning the neutral face space to its happy counterpart.

At block 270, the reconstruction can be output by the display module 128 to a user or other computing device, via the user interface 106 or network interface 110, respectively.

In some embodiments, the method for image reconstruction 200, including representational space estimation, can be conducted for separate time windows of the ERP trace as well as for temporally cumulative data.

Figure 3:
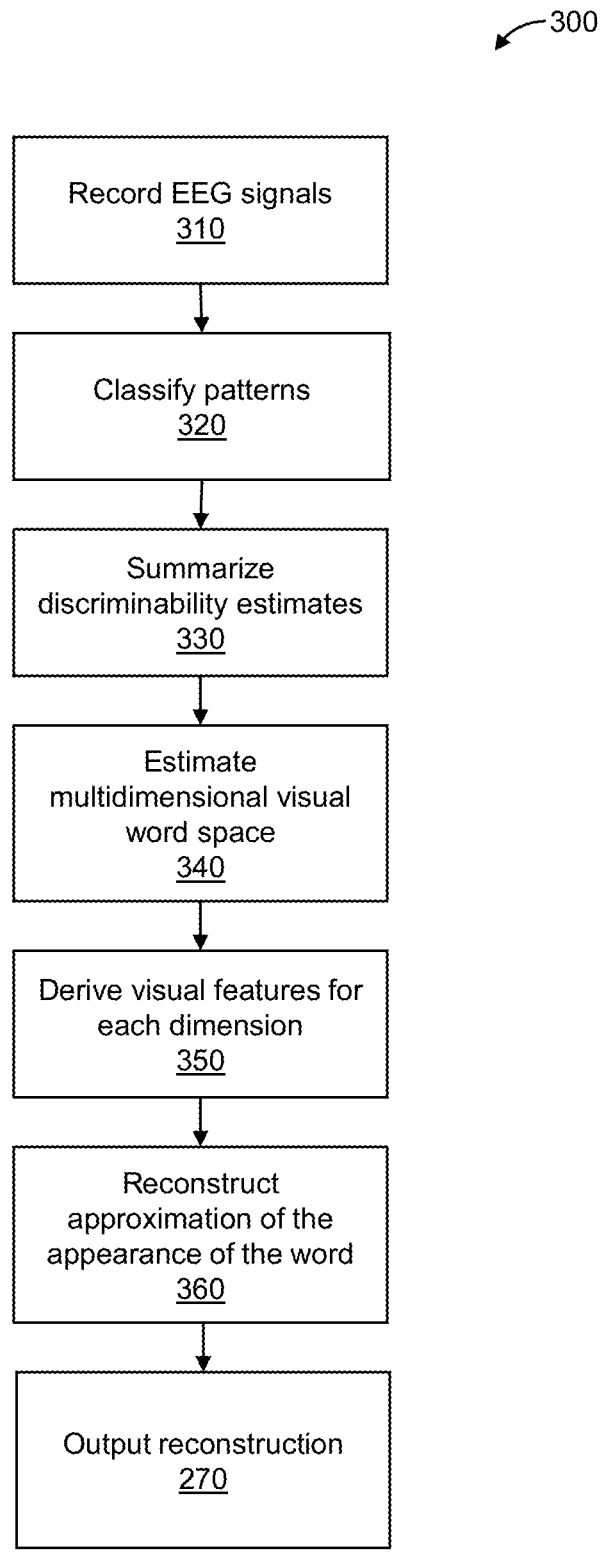
FIG. 3 illustrates a flow diagram of a method for word image reconstruction, according to an embodiment.

FIG. 3 illustrates a method for visual word reconstruction 300, in accordance with an embodiment. In this embodiment of the system 100, as part of the method 300, the system 100 can reconstruct a visual word from EEG signals.

At block 310, the input module 126 receives and records EEG signals from the EEG system 140 via the capture interface 108 across multiple electrodes for each word. The EEG system 140 may receive and record EEG data using, for example, a 64-electrode Biosemi ActiveTwo EEG recording system. In an example, the electrodes can be arranged according to the International 10/20 System. In an example, the electrode offset can be kept below 40 mV. The EEG system 140 or the input module 126 can low-pass filtered the EEG data; for example, using a fifth order sinc filter with a half-power cutoff at 204.8 Hz. The EEG system 140 or the input module 126 can digitize the EEG data; for example, at 512 Hz with 24 bits of resolution. In some cases, the EEG data can be digitally filtered; for example, offline using a zero-phase 24 dB/octave Butterworth filter with a bandpass of 0.1-40 Hz. As described herein, in some cases, EEG data can be separated into epochs by the input module 126.

After removing artifacts and/or false alarms, a range of 75%-100% of trials (across participants) may be selected for further analysis.

In an exemplary setup, twelve electrodes situated over homologue occipitotemporal areas (P5, P7, P9, PO3, PO7, O1 on the left and P6, P8, P10, PO4, PO8, O2 on the right) may be selected for ERP analysis. Their selection can be motivated by the relevance of these electrodes for visual word processing (e.g., from results obtained from word processing). EEG data from electrodes over the left hemisphere and right hemisphere can be averaged by the input module 126, separately creating two sets of signals, one for each hemisphere.

In some cases, for example where there are univariate tests, the EEG data can be averaged by the input module 126 for each unfamiliar visual word identity presented to a subject across expressions. The P1, N170, and N250 components can be identified, either visually or automatically, on a grand-average plot. Two-way repeated measures ANOVA over visual word identities and hemispheres can be conducted on maximum amplitudes; for example, in the 70-180 ms range for P1, and on minimum amplitudes in the 160-250 and 260-350 ms ranges for N170 and N250, respectively. In some cases, Greenhouse-Geisser correction can be applied in case of violation of the sphericity assumption.

At block 320, the classification module 122 classifies patterns across the corresponding EEG signals. In some cases, in order to classify the patterns, epochs may be, for example, linearly detrended, z-scored across time and electrodes, and corrected for outliers (for example, values exceeding three standard deviations from the mean thresholded at ±3 to minimize the deleterious effect of extreme values on pattern classification). In some cases, the epochs may be normalized to the same range (for example, 0-1) and mean (for example, 0.5). In some cases, in order to boost signal-to-noise ratio (SNR) of spatiotemporal patterns, multiple epochs pertaining to a same condition (i.e., same viewed stimulus or same recalled image) may be averaged into ERP traces. In a particular case, all epochs corresponding to the same image stimulus, for a maximum of 4 epochs, may be averaged together resulting in 16 separate traces per stimulus. Advantageously, this approach can also be useful for handling missing data following epoch removal and in balancing the number of observations for pattern classification. Specifically, since it is possible that epochs associated with a given stimulus be removed (e.g., due to artifacts), in some cases this can lead to different numbers of epochs for different stimuli. However, in some cases, averaging data across consecutive epochs (i.e., 1-4 epochs per stimulus following data removal) may ensure that equal numbers of observations can be constructed for each pair of stimuli undergoing pattern classification. As described herein, in some cases, to increase robustness of pattern analyses, epochs may be divided into temporal windows containing multiple conceptual bins.

The classification module 122 can perform the classification using pairwise discrimination of visual word identity/category. In some cases, the discrimination module 124 can use linear Support Vector Machine (SVM) classification (c=1). In some cases, cross-validation can be used; for example, leave-one-out cross-validation (e.g., one out of 16 pairs of observations can be systematically left out for testing while the remaining 15 are used for training). In an example, the SVM can be trained using EEG-based observations corresponding to 1485 pairs of stimuli (i.e., each possible pair out of 55 stimuli) using a leave-one-out cross-validation approach. In this case, classification accuracy can be obtained for each pair by averaging across the iterations. For example, in some cases, classification can be conducted for every pair of words in two ways: (a) within font/letter case, the classifier is trained separately on different types of font/case and tested separately for each; and (b) across font/case, the classifier is trained on one type of font/case and tested on the other. Significance of classification accuracy can be assessed, for example, via a permutation test, by randomly shuffling identity labels (for example, for individual 1) a sufficient number of times (for example, $10^3$ times. While the present embodiment describes using an SVM, it is understood that any suitable machine learning technique or approach can be used; for example, other classification methods based on linear discrimination analysis or neural networks.

In some cases, the classification may be conducted for data averaged across all or multiple participants (i.e., observations constructed from averaged ERP traces). In further cases, classification can be performed for data from individual participants. In some cases, the significance of the overall classification accuracy can be assessed using, for example, one-sample two-tailed t-tests against chance across participants.

At block 330, the reconstruction module 120 determines word discriminability estimates using a confusability matrix. In a particular case, classification accuracies for each pair of stimulus identities, as determined by pattern classification, can be organized into a confusability matrix in which each cell estimates the discriminability of a pair of words. Thus, the matrix can contain information regarding the similarity and/or dissimilarity of any pair of stimulus identities. In some cases, the values of the cells can be further linearly scaled, for example, between 0 and 1.

In some cases, the reconstruction module 120 can derive representational space constructs; for example, multidimensional spaces in which different neural representations correspond to different points and their pairwise similarity is approximated as their space-dependent distance. For example, metric multidimensional scaling (MDS) can be applied to a confusability matrix to approximate a corresponding lower-dimensional space. In an example, the dimensionality of such spaces can be restricted to 20, which may be sufficient to account for most variance in the data (for example, over 90%). This procedure can be conducted on within category estimates of discrimination; for example, within-expression for faces or within-font for words. For example, the word reconstruction procedure can be conducted separately for each font/case, resulting in separate spaces for words displayed in different font/case. Other techniques of dimensionality reduction such as non-metric MDS or generalized MDS can also be used with the same purpose.

At block 340, the reconstruction module 120 estimates a multidimensional visual word space from the structure of the data. Visual word space invariance to image changes introduced by font or letter case can be determined. In most cases, the extent to which the structure of the space is sensitive to stimulus identity independently of other sources of image variability can be quantified and assessed by the reconstruction module 120. To this end, the fit between homologous spaces (for example, words displayed in lower and upper font) can be estimated by aligning one space to the other, for example via Procrustes transformation, and measuring the badness of fit as the sum of squared errors (SSE) between the two spaces. This estimate can serve to confirm the presence of invariance and assess its robustness. For example, if a significant proportion of space structure is preserved despite image changes, the SSE fit should be better than expected by chance. Significance testing can be conducted, for example, through a permutation test for multidimensional spaces: the labels of each point in one of the two homologous spaces can be randomly shuffled and the resulting space fit to the intact one as above. In an example, this procedure can be carried out for a total of $10^3$ permutations, by leaving intact each of the two spaces half of the time while permuting the other space, and permutation-based SSE estimates can be determined each time. Image-invariant information, quantified and identified in this manner, can be used to constrain future reconstructions (i.e., as a prior) irrespective of image variability (e.g., due to font or case).

At block 350, the reconstruction module 120 determines visual features for each dimension. Advantageously, the reconstruction module 120 can capitalize on the structure of neural-based representational space for the purpose of feature derivation and image reconstruction. For example, the reconstruction module 120 can capture spatiotemporal information in EEG patterns and determine the ability of invariant visual information to support image reconstructions of word identity. In a particular case, the reconstruction module 120 can conduct this determination as follows: initially derive visual features for each dimension of EEG-based representational space; identify subspaces relevant for reconstruction purposes; and estimate the coordinates of a reconstruction target.

As described herein, the reconstruction module 120 may separately derive visual features accounting for representational space topography for each dimension of EEG-based representational space. A similar procedure can be followed to the one described herein for the case of grayscale targets such as words, except that each CIM feature can consist in a single image rather than a CIEL*a*b* triplet.

As described herein, in some cases, the reconstruction module 120 can identify subspaces relevant for reconstruction purposes using feature and/or dimension selection, since not all dimensions may encode systematic visual information. As described herein, in some cases, the reconstruction module 120 can estimate the coordinates of a target visual word in a type-specific visual word space, as described herein.

At block 360, the reconstruction module 120 reconstructs an approximation of the appearance of each word (referred to as a "target word") through the combination of the visual features. The reconstruction module 120 can construct the target word through a linear combination of significant CIMs. Relevant CIMs, as identified through feature selection above, can be multiplied with the target's coordinates in the representational space for the dimension corresponding to each CIM. CIMs can be normalized under specific constraints (e.g., proportional to the percentage of variance explained by each corresponding dimension) and summed together. This sum can be added to an average word obtained from all remaining non-target items and playing the role of a prior. The resulting image can be further normalized (e.g., with a set luminance average and contrast in case this is already known or derived independently from the data). Advantageously, this approach can capitalize on visual word space invariance for reconstruction purposes. Specifically, a capital letter version of visual word space can be aligned to its lowercase letter counterpart via, for example, Procrustes transformation using all but one visual word. The remaining visual word from the capital letter version of visual word space can be projected into the lowercase letter space using, for example, the parameters of the Procrustes mapping function found above. In this case, the resulting coordinates in lowercase letter visual word space can be used to reconstruct the appearance of the target visual word, with lowercase letters, from lowercase letter CIMs. In further cases, a capital letter version of the target visual word can rely on aligning the lowercase letter visual word space to its capital letter counterpart.

At block 370, the reconstruction can be output by the display module 128 to a user or other computing device, via the user interface 106 or network interface 110, respectively.

FIG. 4A provides three separate examples of reconstructions of facial images with neutral expressions 400 determined experimentally, using the system 100, along with estimates of accuracy. The column of three facial images on the left are examples of faces with neutral expressions as viewed by participants (i.e., stimuli). The column of the three images on the right are reconstructions from EEG data (i.e., reconstructions). Numbers in the top corners of each reconstruction mark estimates of accuracy according to two different criteria (computer-based on the upper-left and human-based on the upper-right).

FIG. 4B provides three separate examples of reconstructions of facial images with happy expressions 450 determined experimentally, using the system 100, along with estimates of accuracy. The column of three facial images on the left include those with happy expressions as viewed by participants (i.e., stimuli). The column of three images on the right are reconstructions from EEG data (i.e., reconstructions). Numbers in the top corners of each reconstruction mark estimates of accuracy according to two different criteria (computer-based on the upper-left and human-based on the upper-right).

Figure 5A:
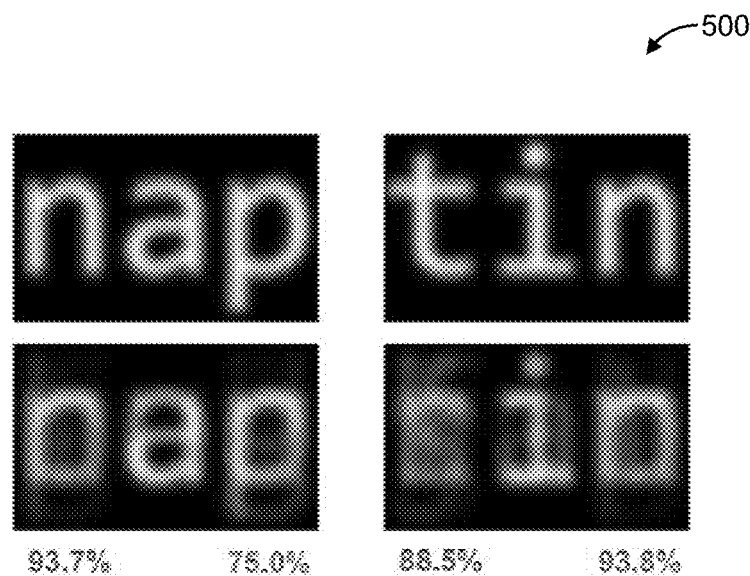
FIGS. 5A and 5B illustrate reconstructions of word images, along with estimates of their accuracy.
Figure 5B:
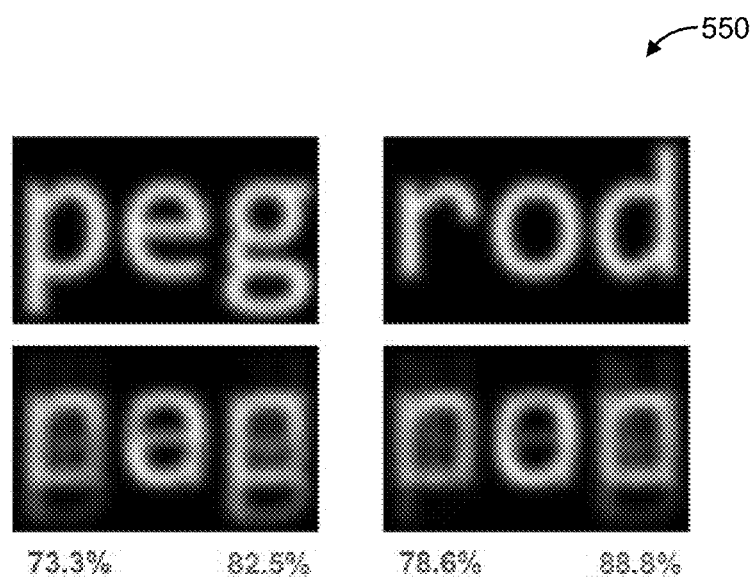

FIG. 5A provides two examples of reconstructions of word images 500, determined experimentally, using the system 100, along with estimates of accuracy. These word images include those viewed by participants (top row) and corresponding reconstructions from EEG data (bottom row) using the system 100. Numbers displayed under each reconstruction represent estimates of accuracy according to two different criteria (computer-based on the left and human-based on the right). FIG. 5B provides another two examples of reconstructions of word images 550, determined experimentally, using the system 100, along with estimates of accuracy, in the same manner as in FIG. 5A.

Figure 6A:
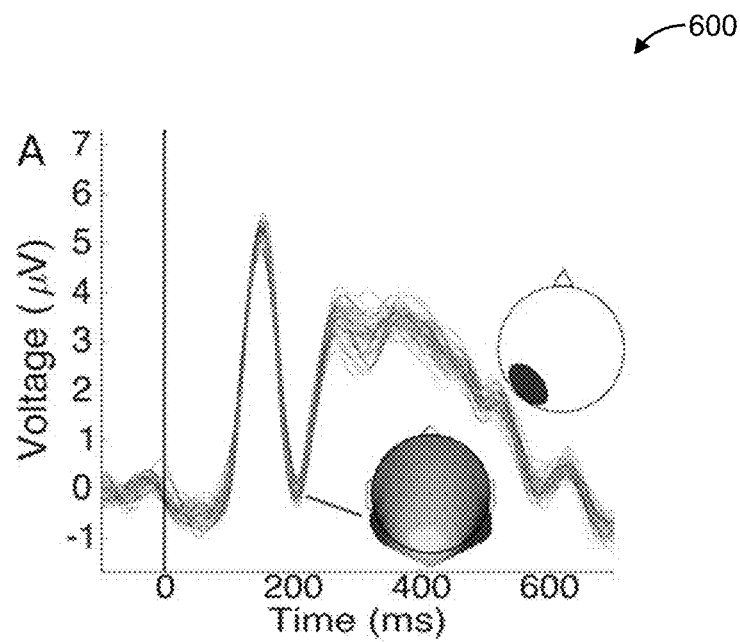
FIGS. 6A and 6B illustrate graphs showing grand-averaged event-related potentials (ERPs)
Figure 6B:
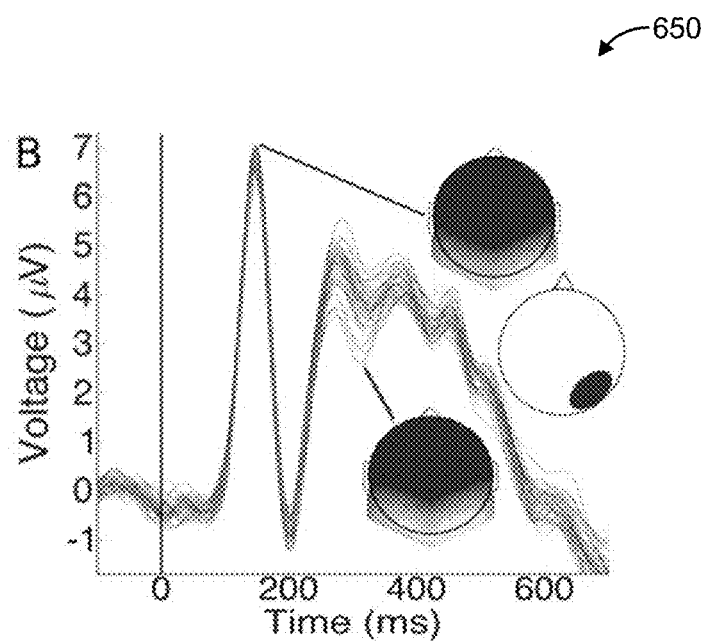

FIGS. 6A and 6B illustrate graphs showing examples of ERPs, determined experimentally, using the system 100. In FIG. 6A, there is a graph of grand-averaged ERPs across left hemisphere electrodes 600 (P5, P7, P9, PO3, PO7, O1) of a subject for 54 facial identities (averaged across expressions). Head maps show voltage distributions at N170. In FIG. 6B, there is a graph of grand-averaged ERPs across right hemisphere electrodes 650 (P6, P8, P10, PO4, PO8, O2) for 54 facial identities (averaged across expressions). Head maps show voltage distributions at P1, N250.

Figure 7A:
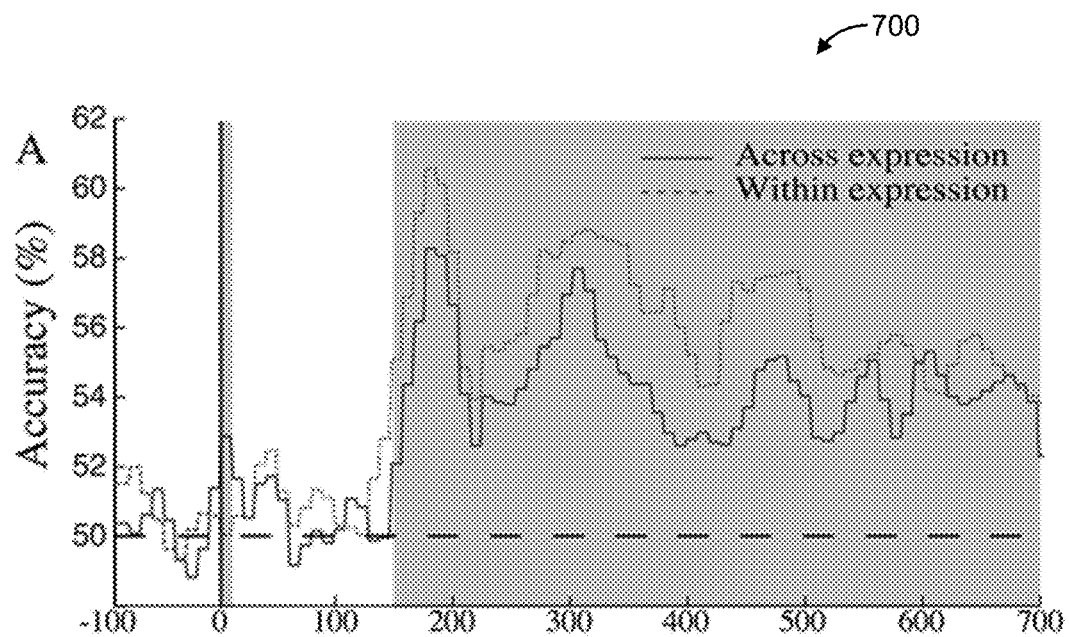
FIGS. 7A and 7B illustrate graphs that show the time course of EEG-based classification accuracy for across and within-expression discrimination of facial identity.
Figure 7B:
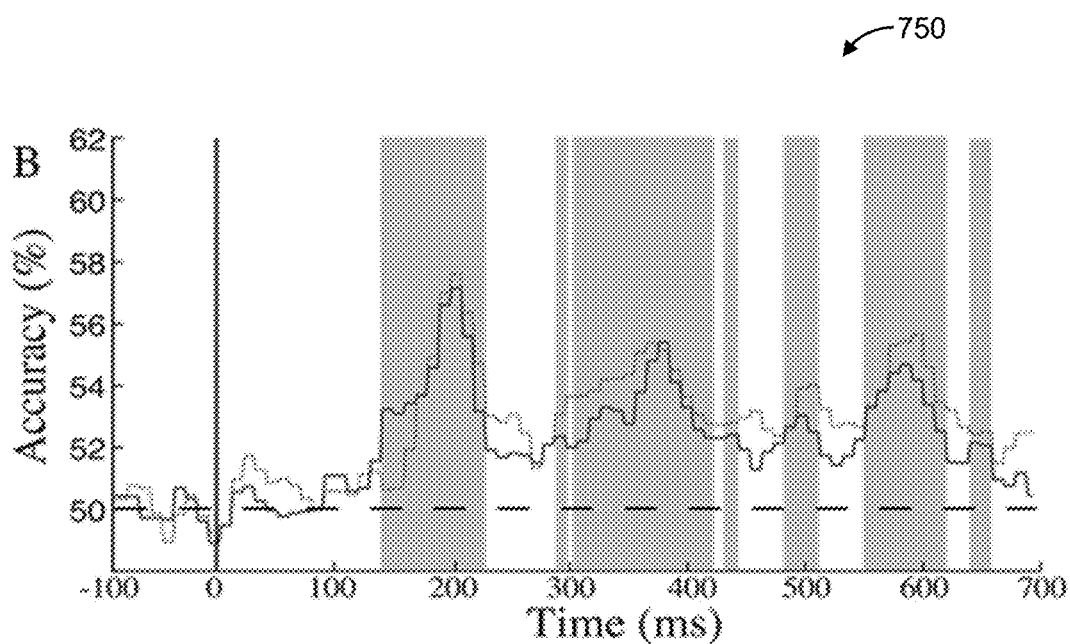

FIG. 7A illustrates a graph that shows an example of a time course of EEG-based classification accuracy for across-expression and within-expression discrimination of facial identity 700, determined experimentally, using the system 100. Classification was conducted across consecutive 10 ms window patterns over 12 occipitotemporal electrodes for group-based ERP data. Both types of analysis exhibited above-chance discrimination across extensive temporal intervals (permutation test; FDR-correction across time, q<0.01). Shaded areas mark intervals of better-than-chance discrimination for across-expression classification. FIG. 7B illustrates a graph that shows an example of a time course of EEG-based classification accuracy for across-expression and within-expression discrimination of facial identity for a single representative participant 750, determined experimentally, using the system 100. Classification was conducted across consecutive 10 ms window patterns over 12 occipitotemporal electrodes. Both types of analysis exhibited above-chance discrimination across extensive temporal intervals (permutation test; FDR-correction across time, q<0.01). Shaded areas mark intervals of better-than-chance discrimination for across-expression classification.

Figure 8:
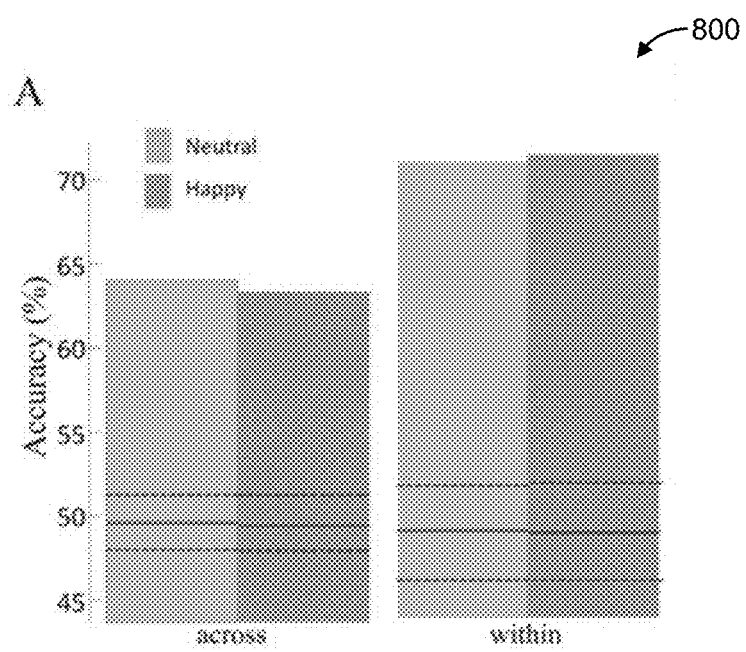
FIG. 8 illustrates a graph showing EEG-based classification accuracy for across and within-expression discrimination of facial identity with temporally cumulative data.

FIG. 8 illustrates graphs showing examples of EEG-based classification accuracy for across-expression and within-expression discrimination of facial identity with temporally cumulative data (50-650 ms after stimulus onset), determined experimentally, using the system 100. In FIG. 8, there is a plot showing accuracy corresponding to neutral and happy faces for group-based ERP data 800. In graph 800, the plots display the results of permutation tests (solid and dashed horizontal lines indicate average accuracy and 99% confidence intervals estimated with $10^3$ permutations). The plots illustrate that reconstruction accuracy is well above chance and the overall performance of the embodiments described herein is quite robust (especially in the case of within-expression reconstructions).

Figure 9A:
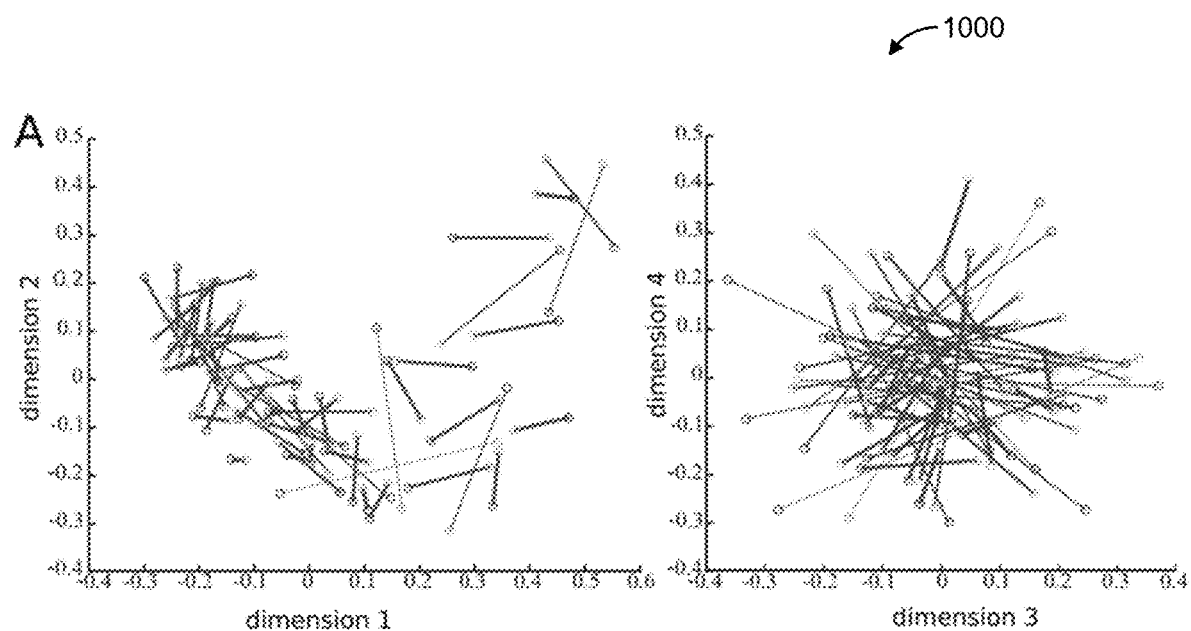
FIG. 9A illustrates a graph showing neutral and happy face space estimates along with their fit.
Figure 9B:
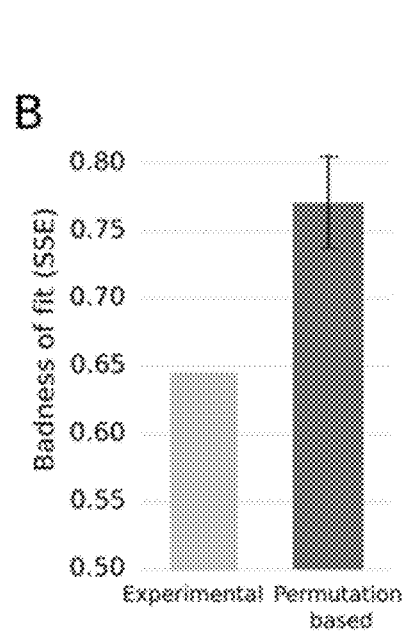
FIG. 9B illustrates a histogram showing badness of fit for the two spaces (i.e., neutral and happy face) compared to their permutation-based counterpart.

FIG. 9A illustrates a graph showing examples of neutral and happy face space estimates along with their fit 1000 (after Procrustes alignment), determined experimentally, using the system 100. Estimates were derived through MDS analysis of similarity matrices based on within-expression face discrimination of group-based temporally cumulative data. The two face space estimates exhibited a similar topography as found with their visualization across multiple dimensions. Red and green circles (colors not shown) indicate neutral and happy faces, respectively. Solid lines connect face images with the same identity with the thickness of the line proportionally reflecting shorter distances. The first four dimensions shown here account for 40% and 41% variance for neutral and happy face space. FIG. 9B illustrates a graph showing an example of badness of fit (sum of squared errors) for the two spaces compared to their permutation-based counterpart 1050 (average fits and 95% confidence intervals estimated with $10^3$ permutations).

FIG. 10A shows examples of classification images (CIMs) extracted from EEG-based face space constructs for neutral faces 1100, determined experimentally, using the system 100. FIG. 10B shows examples of classification images (CIMs) extracted from EEG-based face space constructs for happy faces 1150, determined experimentally, using the system 100. In both figures, pairs of images show raw CIMs (odd columns) and their analysis (even columns) with a pixelwise permutation-based test (FDR-corrected across pixels; q<0.05). Various analyzed areas of the captures faces have been found to be brighter (L*), redder (a*), or more yellow (b*) than chance in CIEL*a*b*. The exemplary results shown are separate for the first and fourth dimensions of face spaces derived from group-based temporally cumulative data.

Figure 11A:
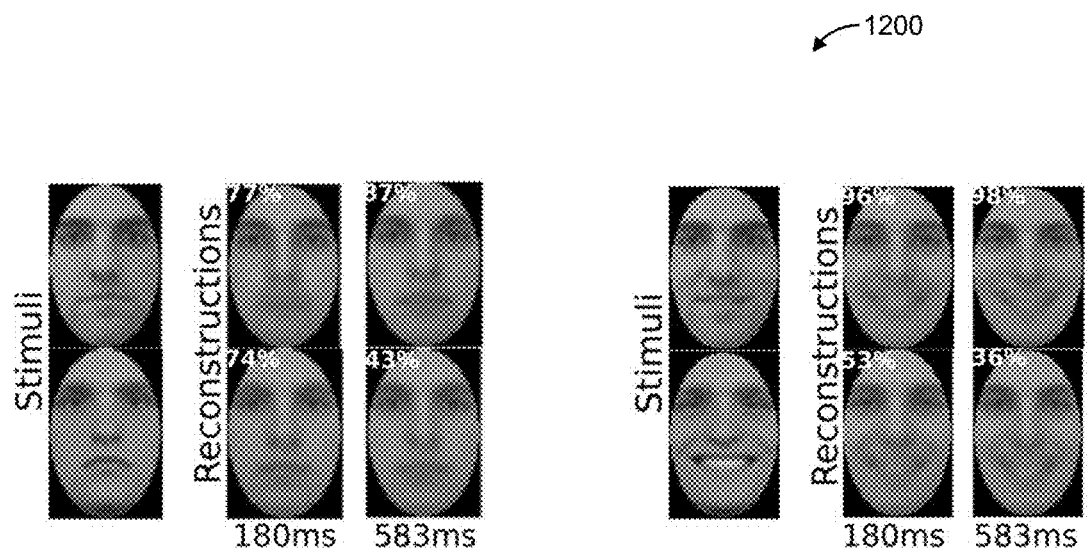
FIGS. 11A and 11B illustrate reconstruction results for neutral and happy face images across consecutive 10 ms windows of group-based data.
Figure 11B:
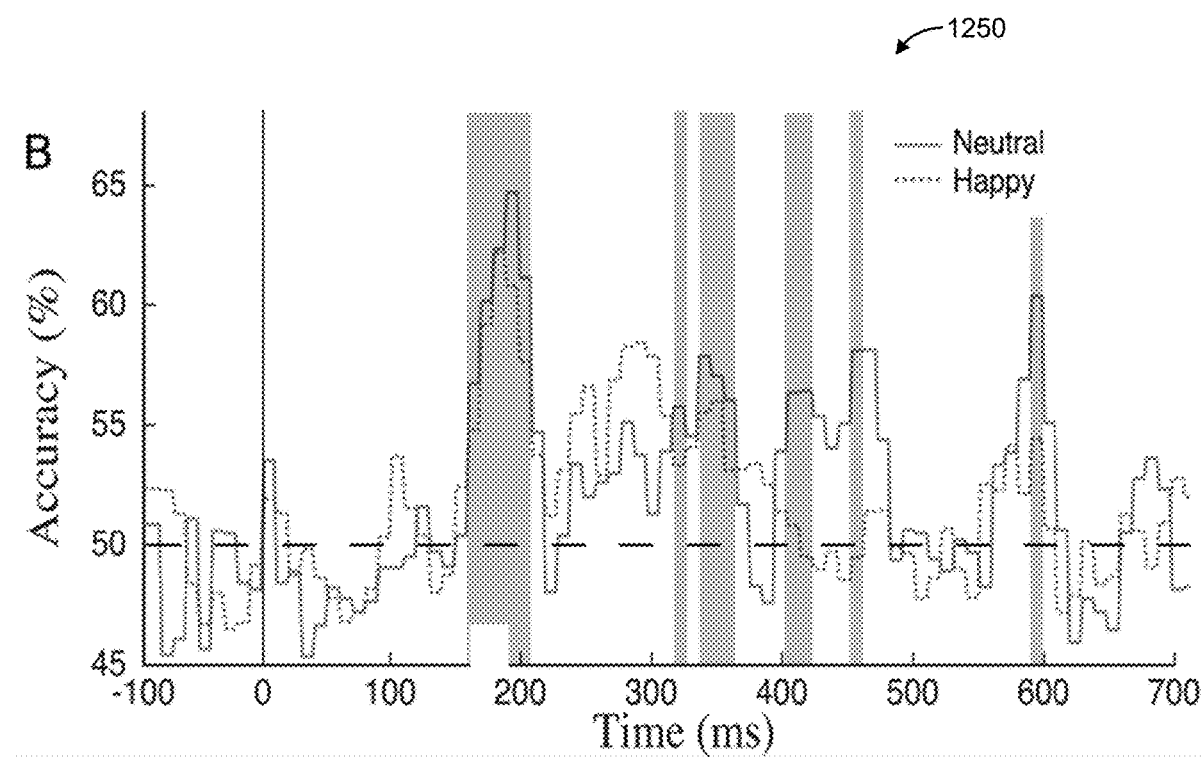

FIGS. 11A and 11B illustrate examples of reconstruction results for neutral and happy face images across consecutive 10 ms windows of group-based data, determined experimentally, using the system 100. FIG. 11A provides examples of face stimuli along with their corresponding reconstructions at two different times 1200 (numbers in the upper left corner indicate image-based estimates of reconstruction accuracy). The reconstructions can be formatted by converting them from CIEL*a*b* back to RGB. In FIG. 11B, a graph is shown that illustrates an example of a time course of reconstruction accuracy 1250. Both neutral and happy face images exhibit above-chance discrimination across multiple temporal intervals (permutation test; FDR correction across time, q<0.05; shaded areas mark intervals of better-than-chance discrimination for neutral faces). Reconstruction accuracy is maximized in the vicinity of the N170 component (as shown in FIG. 6A) and of the discrimination peak found with pattern classification (as shown in FIGS. 7A and 7B).

Figure 12A:
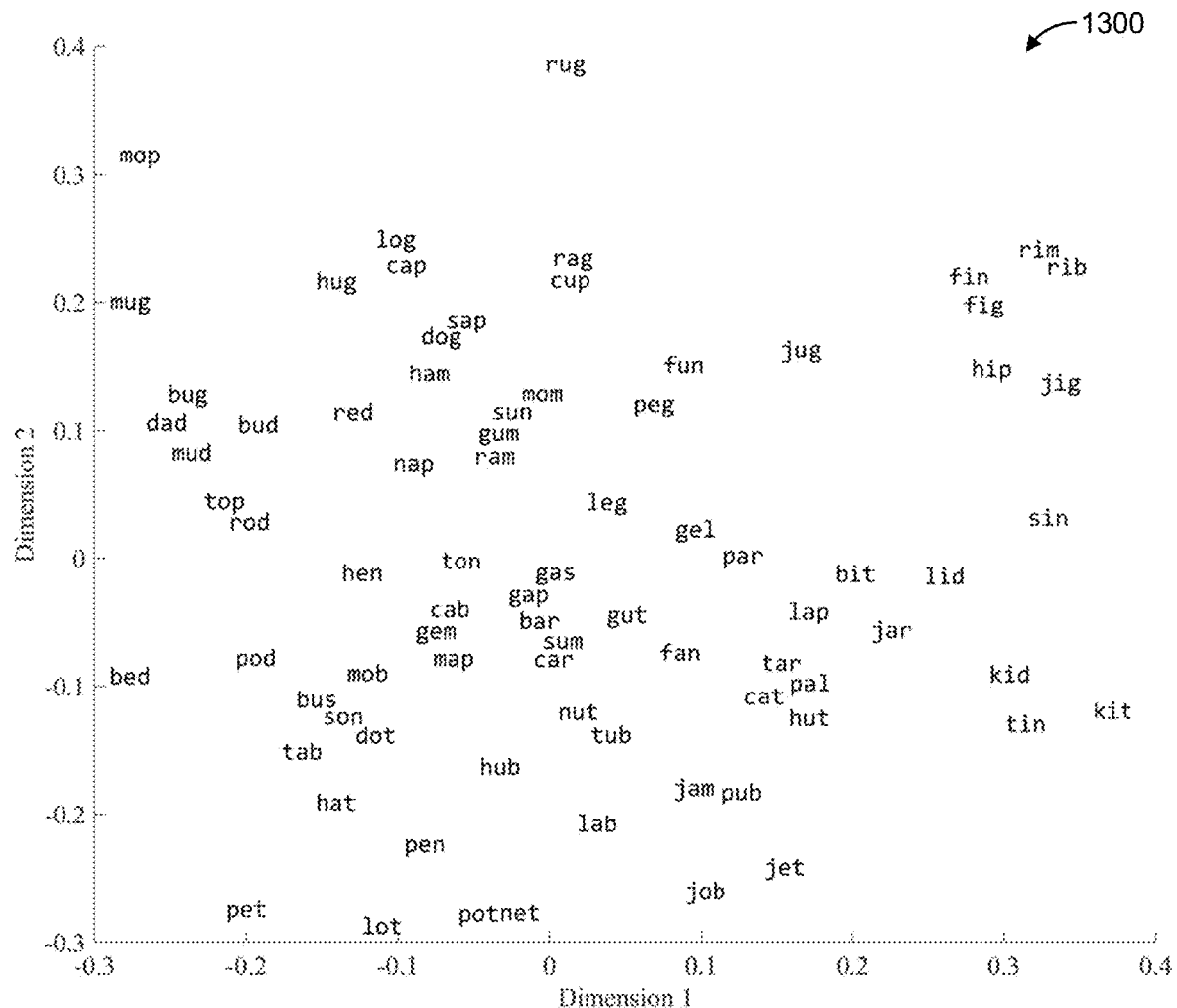
FIGS. 12A AND 12B illustrate an example of EEG-based visual word space and classification images (CIMs) extracted from this space.
Figure 12B:
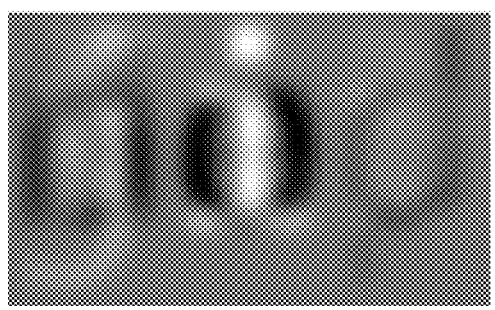
Figure 12B:
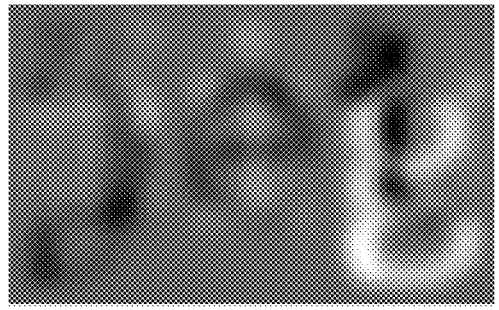

FIG. 12A shows an example of visual word space 1300 derived from group-based EEG temporally cumulative data using the system 100 (only 2 dimensions are shown for convenience). FIG. 12B shows an example of classification images (CIMs) extracted from two dimensions of that space.

The following describes an exemplary experimental approach used by the present inventors to illustrate the described output of the system 100; for example, to arrive at the data shown in FIGS. 4A to 12B. This approach was used to derive face space constructs from the EEG signal associated with consecutive time windows separately for different facial expressions (i.e., neutral and happy). The experimental approach provides exemplary experimental design, exemplary results and outcomes, and provides at least some of the experimental basis for at least some of the embodiments described herein.

Participants and Stimuli

Thirteen healthy adults (6 males, 7 females; age range: 18-27 years) with normal or corrected-to-normal vision were recruited from a community to participate in the experiment.

A total of 140 face images of 70 individuals, each displaying a neutral and a happy expression were used as experimental stimuli. Out of these, 108 images of 54 unfamiliar males were selected from three databases. The remaining 32 images displayed faces of 6 famous male and 10 female individuals selected from open access sources. In this experiment, unfamiliar male face stimuli were the focus, while female faces were used as go trials in a go/no-go gender recognition task, and additional famous male faces were included to promote alertness.

All images featured young adult Caucasian individuals with frontal view, gaze, and illumination. The stimuli were selected so that no facial accessories, hair, or makeup obscured the internal features of the face and so that all happy expressions displayed an open-mouth smile. These images were: (a) scaled uniformly and aligned with roughly the same position of the eyes and the nose; (b) cropped to eliminate background; (c) normalized with the same mean and root mean square (RMS) contrast values separately for each color channel in CIEL*a*b* color space, and (d) reduced to the same size (95×64 pixels).

Experimental Design

Prior to EEG testing participants were administered the Cambridge Face Memory Test (CFMT) to confirm that their face processing abilities fell within the range of normal performance for young adults. Participants also completed the Vividness of Visual Imagery Questionnaire 2 (VVIQ-2) along with a custom familiarity-rating famous face questionnaire.

During EEG sessions, participants were seated in a dimly lit room at a viewing distance of 80 cm from an LCD monitor (resolution: 1920×1080, refresh rate: 60 Hz). The participants were instructed to perform a go/no-go gender recognition task by pressing a designated key every time they saw a female face, irrespective of expression. The experiment consisted of 32 blocks of stimulus presentation divided into 2 sessions carried out on different days. In each session, experimental blocks were preceded by one training block, subsequently discarded from all analyses. The blocks were separated by self-paced breaks.

Over the course of any given block, each image of a male face was presented twice and each image of a female face was presented once, for a total of 260 trials. Images were presented in a pseudorandom order under the constraint that no facial identity would appear consecutively. Each stimulus was presented in the center of the screen against a black background and subtended a visual angle of 3.2×4.9. A stimulus display lasted for 300 ms and it was followed by a fixation cross for a duration ranging randomly between 925-1075 ms. Each session, including participant and equipment setup, lasted around 2.5 hours.

The procedure above, including face space estimation, was conducted for separate time windows of the ERP trace as well as for temporally cumulative data.

Evaluation of Reconstruction Results

Image reconstructions were compared to their target stimuli via two different approaches. First, image-based accuracy was estimated as the percentage of instances for which a reconstructed image in CIEL*a*b* was more similar to its target, by a pixel-wise L2 metric, than to any other stimulus with the same expression. Average reconstruction accuracy was then compared against permutation-based chance estimates by shuffling reconstruction labels and by recomputing average accuracy across reconstructions each time (for a total of 103 permutations). This procedure was applied to all types of reconstruction (e.g., both window-based and temporally cumulative) separately for neutral and happy faces.

Second, a single set of reconstructions, based on temporally cumulative group-based data, was subjected to experimental evaluation in a separate behavioral test. To this end, 14 new participants (six males and eight females, age range: 20-28) were requested to match image reconstructions to their targets in a two-alternative forced choice (2AFC) task. Specifically, each of 108 unfamiliar face reconstructions, including both expressions, was presented in the company of two stimuli, one of which was the actual target and the other was a foil (another face image). Thus, on each trial, a display was shown containing a reconstructed image, at the top, and two stimuli side by side, at the bottom, all of which had the same expression and the same size (as specified in Experimental Procedures). Each display was presented until participants made a response to decide which stimulus was more similar to the top image by pressing a designated left/right key. For each participant, any reconstructed image was presented 4 times in the company of different foils; thus, across participants, all 53 possible foils for a given reconstruction were exhausted. Stimulus order was pseudo-randomized so that different reconstructed images appeared on consecutive trials while target stimuli appeared equally often on the left/right side.

Experimental-based estimates of reconstruction accuracy were measured as the proportion of correct matches across participants and tested for significance tested against chance (50%) using a one-sample two-tailed t-test. Experimental and homologous image-based estimates of reconstruction accuracy were compared to each other via Pearson correlation across images, separately for neutral and happy faces.

Pattern Classification of Facial Identity

A total of 108 unfamiliar male faces (54 individuals×2 emotional expressions) were classified based on ERP traces associated with their viewing. Specifically, spatiotemporal ERP patterns across bilateral occipitotemporal electrodes were averaged across participants and, then, evaluated for their ability to support facial identity discrimination. To assess the time course of individual face processing, classification was conducted across consecutive 10 ms temporal windows both within and across expression by training and testing the classifier on faces with the same or different expression.

This analysis found significant levels of discrimination across extensive intervals (permutation test; q<0.01). Specifically, across-expression classification evinced above-chance accuracy from 152 ms after stimulus presentation until the end of the epoch, with two peaks at 170 ms and 295 ms (see FIG. 7A). Within-expression classification yielded a similar time course but consistently higher levels of accuracy and an earlier onset, at 140 ms, in agreement with the reliance on additional, lower-level image cues for this type of discrimination. In addition, an earlier interval of significance was found for across-expression classification between 0-5 ms; however, given its very early occurrence, its reduced amplitude, and the absence of its replication by within-expression classification, this data point is treated as a false positive. Of note, for both types of classification, it was found that discrimination accuracy was maximized in the vicinity of the N170 component as identified by univariate analyses of ERP data (see FIGS. 6A and 6B).

Single-participant analyses was also conducted. These analyses confirmed the feasibility of facial identity discrimination from the data of single participants (see FIG. 7B). However, in some cases, discrimination levels may be lower than in the group-based analyses, likely due to the lower signal-to-noise ratio (SNR) of single-participant ERPs and its impact on classification. There may also be multiple intervals of discrimination, as opposed to a single, uninterrupted one.

Pattern classification was applied to temporally cumulative data by concatenating data points from all time bins between 50 ms-650 ms after stimulus onset. The aim of this analysis was to maximize discrimination performance by concomitantly exploiting relevant information from all potentially relevant time points. Specifically, while the approximately 61-fold increase in pattern dimensionality (i.e., 12 electrodes×307 time bins) would, by itself, reduce the effectiveness of classification, the possibility that any ensuing classification decrement may be offset by the use of complementary sources of information from different time points was also examined.

Consistent with the examination described above, it was found that this analysis yielded robust levels of discrimination for group-based data (see FIG. 8): 64% and 71% for across and within-expression discrimination, respectively (permutation test; p=0.001 for both types of discrimination and both expressions). Of note, these results outperform peak performance obtained with window-based analyses in the proximity of the N170 component. Further, single-participant estimates of discrimination with temporally cumulative data were also computed and averaged across participants (see FIG. 8). Again, performance was better than chance for both within-expression discrimination (two-tailed t-test across participants against 50% chance-level discrimination; t(12)=9.89 and 7.27, Cohen's d=2.1 and 2.86 for neutral and happy faces, respectively; p's=0.001) and for across-expression discrimination (t(12)=6.84 and 7; d=2.02 and 1.97 for neutral and happy faces, respectively;

p's<0.001). Further, a two-way repeated measures analysis of variance (2 discrimination types×2 expressions) revealed a main effect of discrimination types ($F(1,12)=50.05$, $p<0.001$, $\eta_p^2=0.81$), with higher accuracy for within than across-expression discrimination, but no effect of expression and no interaction.

To examine possible effects of the database of faces used, the analysis above was repeated while restricting pattern classification either to pairs of faces from the same database or from different databases. A two-way repeated measures analysis of variance (2 discrimination types: within/across expression×2 pair types: within/across database) was carried out to this end, classification estimates were collapsed across neutral and happy faces given the absence of any expression effects above. This analysis revealed a main effect of discrimination types ($F(1,12)=45.92$, $p<0.001$, $\eta_p^2=0.79$), with higher accuracy for within than across-expression discrimination, as well as a main effect of pair types ($F(1,12)=38.73$, $p<0.001$, $\eta_p^2=0.76$), with higher accuracy for within than across-database classification. Critically though, all classification estimates were significantly above chance (two-tailed t-tests against 50% chance-level discrimination); mean accuracy=56.3%, $t(12)=8.36$, $p<0.001$, Cohen's $d=2.32$ for within-expression, within-database discrimination; mean accuracy=58.7%, $t(12)=8.38$, $p<0.001$, Cohen's $d=2.32$ for within-expression, across-database discrimination; mean accuracy=53.9%, $t(12)=7.64$, $p<0.001$, Cohen's $d=2.12$ for across-expression, within-database discrimination; mean accuracy=55.9%, $t(12)=6.88$, $p<0.001$, Cohen's $d=1.91$ for across-expression, across-database discrimination).

Classification analyses also included repeating all face pairs within and across databases with all 64 electrodes, instead of the subset of 12 occipitotemporal electrodes noted above. In this case, no consistent boost in discrimination was found for any analysis in this case; and thus, the results were sufficient based on occipitotemporal electrodes only.

Neural-Based Face Space and Expression-Invariance

Face space estimates were derived through the application of MDS to within-expression face classification of temporally cumulative data. Specifically, MDS was applied to pairwise face discrimination values derived through pattern analysis of group-based data, separately for neutral and happy faces. The resulting spaces were reduced to the first 20 dimensions and aligned with each other via Procrustes transformation.

An examination of the resulting spaces for neutral and happy faces, following their alignment, was consistent with the presence of a common topography across expressions (see FIG. 9A). To assess their fit more rigorously, a comparison with permutation-based alignment estimates (see FIG. 9B) was computed. This comparison indicated that the fit between the two spaces was considerably better than chance ($p<0.001$). Advantageously, this finding allowed the present inventors to exploit the structure of visual information invariant across expression for reconstruction purposes, as detailed herein.

Reconstruction Results

Visual features were derived from the structure of face space, dimension by dimension. Such features, or classification images (CIMs), were assessed through a permutation test for the presence of significant information pixel-by-pixel separately for each CIEL*a*b* color channel.

An examination of CIMs containing significant information revealed global contrast patterns across multiple color channels (see FIGS. 10A and 10A). The emergence of these features confirmed that neural-based face space is, at least partly, organized by visual information (as opposed, for instance, to higher-level semantic information). Thus, CIMs were determined by the present inventors to be useful as reconstruction features.

Accordingly, significant CIMs were linearly combined to deliver an approximation of face appearance broadly following an image reconstruction approach recently used with fMRI data. Specifically, image reconstruction was separately applied to neutral and happy expressions. Thus, the common face space topography for the two expressions can allow using the relative position of a given identity in one space to deliver a reconstruction of the same facial identity with the opposite expression.

The above procedure, as performed for separate time windows with group-based data, found evidence for multiple intervals capable of supporting above-chance reconstruction (image-based permutation test; $q<0.05$). Reconstruction accuracy was assessed via a pixelwise image-matching test across reconstructed images and stimulus images. The earliest interval had an onset at 160 ms and 170 ms for neutral and happy faces, respectively, while accuracy peaked at 187 ms and 180 ms for the two expressions (see FIG. 11B).

Figure 13:
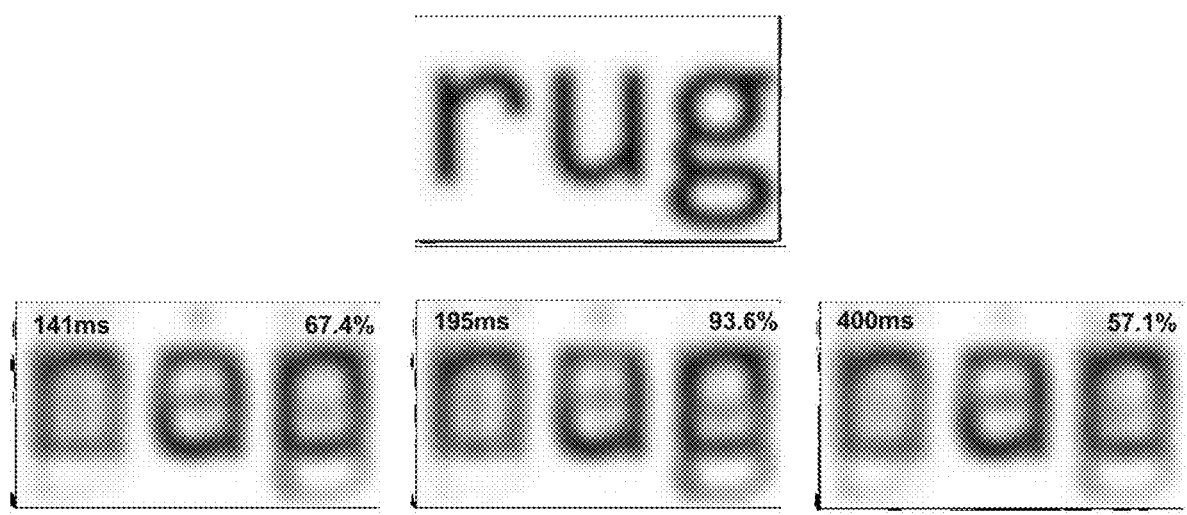
FIG. 13 is an example of a word stimulus reconstruction target (top) compared to three reconstructed frames along with corresponding reconstruction accuracy.
Figure 14:
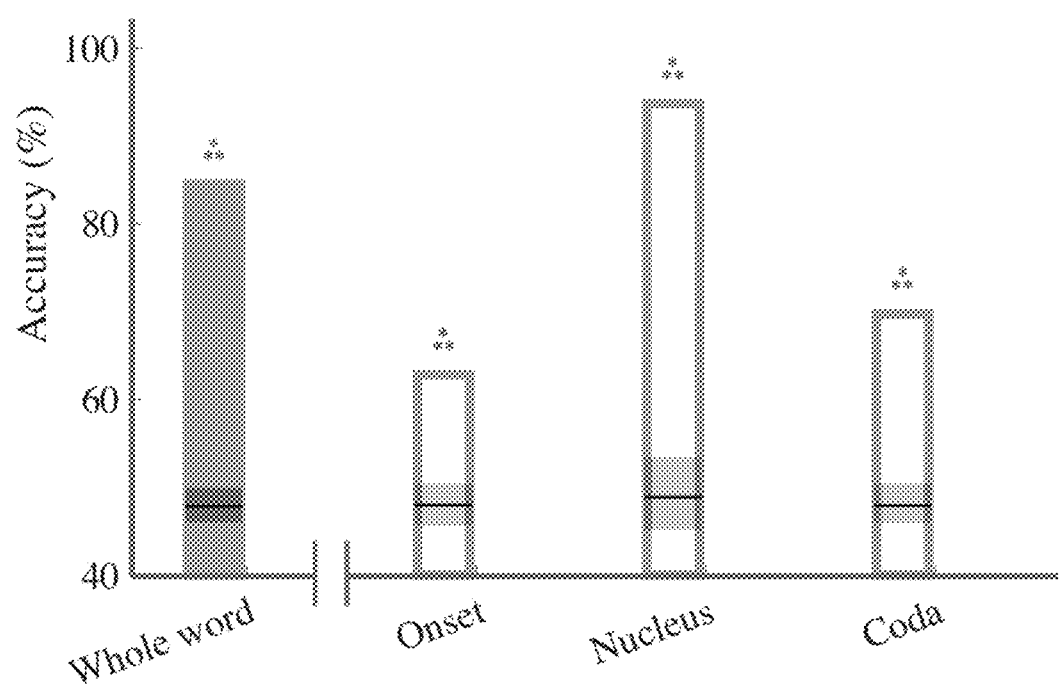
FIG. 14 is a graph showing an example of reconstruction accuracy for words and for each letter separately.

A representative example of image reconstruction, interval by interval, is shown in a 'Movie 1' along with the temporal profile of its reconstruction accuracy. FIG. 13 shows an example of Movie 1, whereby the top image illustrates the reconstruction target (word stimulus) and the low images show frames of Movie 1 with indications of time in milliseconds (after stimulus presentation) along with the corresponding reconstruction accuracy. FIG. 14 illustrates reconstruction accuracy for words, as well as for each letter separately, for the example of Movie 1; where onset is the 1st letter of the word, nucleus is the 2nd, and coda is the 3rd. Horizontal segments on each bar and shaded areas indicate chance-level performance and variability. Overall, the plots illustrate that reconstruction for this example is well above chance ($p<0.001$) for words and also for letters (especially for the nucleus).

The application of the above procedure to temporally cumulative data was determined to have more robust results: 69.46% image-based accuracy for neutral faces and 63.91% for happy faces (permutation test; $p$'s=0.001) (see FIG. 8). Experimental-based estimates of accuracy, obtained with a new group of participants, led to more modest levels of accuracy (see FIG. 11B, described below); however, both neutral and happy face reconstructions were still accurate above chance (two-tailed t-test across participants against 50% chance-level discrimination: $t(13)=6.70$, 4.38; Cohen's $d=1.86$, 1.22, for neutral and happy, respectively; $p$'s<0.001 for all), with no difference between neutral and happy faces. Further, reconstruction accuracies as estimated by the two tests, image-based and experimental-based, were compared with each other across facial identities and were found to significantly correlate with each other ($r=0.43$ and $0.42$; $p$'s=0.001 and 0.002 for neutral and happy faces, respectively), thus, mutually reinforcing their validity.

Across-expression classification estimates obtained with temporally cumulative data were compared with their corresponding reconstruction accuracies averaged across expressions. Specifically, Pearson correlation across facial identities found a positive relationship between across-expression discrimination and image-based accuracy ($r=0.87$, $p<0.001$). Thus, in some cases, the more discriminable a facial identity is, the more accurately it can be reconstructed.

Reconstruction was performed for single-participant data and evaluated with the aid of the image-based test. Accuracy levels were found to be above chance (two-tailed t-test across participants against 50% chance-level discrimination; mean accuracy=53.1%, t(12)=2.52, p=0.027, Cohen's d=0.73 and mean accuracy=53.3%, t(12)=2.24, p=0.045, Cohen's d=0.65 for neutral and happy face reconstructions, respectively). Pearson correlations between classification accuracy and reconstruction accuracy across participants were also found to be significant (r=0.83 and r=0.84, for neutral and happy faces, respectively; p's<0.001). Thus, in some cases, participants who provided data supporting higher levels of face classification also provided more accurate reconstruction results.

Advantageously, the system 100 allows for EEG-based pattern classification of facial identity across changes in expression from EEG data. Discrimination peaks were identified in the proximity of the N170 and N250 ERP components, consistent with univariate analyses pointing to the relevance of both components for face processing. The onset of discrimination, around 150 ms, was intermediary to early estimates in the vicinity of P1 and later estimates around 200 ms as reported with MEG. In some cases, early estimates, along with higher levels of discrimination, can be triggered by the use of low-level image properties. In line with this consideration, it was found that within versus across-expression discrimination produced earlier and consistently higher levels of discrimination accuracy. Importantly though, across-expression classification, which aims to minimize reliance upon low-level cues, exhibited robust levels of discrimination across an extensive interval (i.e., from −150 ms onwards).

Advantageously, the system 100 can perform temporally cumulative analyses targeted identity discrimination across a broad interval between 50-650 ms after stimulus onset. Despite the increase in dimensionality for the classification patterns, these data supported even more robust levels of accuracy for both within and across-expression discrimination, consistent with the presence of relevant information at multiple time points. Moreover, the superior levels of discrimination obtained with temporally cumulative data, as opposed to 10 ms windows, agrees with the presence of distinct sources of information at different time points. That is, the boost in classification accuracy is related with the ability to exploit complementary information about facial identity at different times. Advantageously, the boost in classification noted above is useful because it suggests that placing less emphasis on clarifying the time course of discrimination can be better served by exploiting patterns across larger temporal intervals. Accordingly, face space structure and image reconstruction can be determined with both window-based and cumulative data.

Advantageously, the system 100 can perform a neural-based estimate of face space constructed from EEG data, using the presence of visual information captured by CIMs. It was determined that pattern discrimination relies, at least partly, on relevant visual information (e.g., as opposed to higher-level semantic cues).

Advantageously, the system 100 can perform image reconstruction with CIM features derived directly from the structure of EEG data; as opposed to other approaches that, for example use predefined visual features selected due to their general biological plausibility. It was found that multiple temporal intervals supported better-than-chance reconstruction for both neutral and happy faces with a peak in the proximity of the N170 component. Also, reconstruction accuracy was further boosted by considering temporally cumulative information, as used for pattern classification. The results are notable in that they exploit invariant face space information for reconstruction purposes. Thus, making use of the visual nature of facial identity representations rather than just to lower-level pictorial aspects of face perception.

Advantageously, the system 100 can perform image reconstruction to neuroimaging modalities without having to use fMRI like in other approaches. It shows that EEG-based reconstruction can have high overall accuracy.

The present inventors have determined, using the system 100, that individual faces can be discriminated from their corresponding EEG patterns, that their time course exhibits an extended interval of significant discrimination, and that multiple discrimination peaks occur, including an early one in the vicinity of the N170 component. It was also found that such discrimination can be performed even with a large, homogenous set of face images controlled for low and high-level face properties (e.g., through geometrical alignment and intensity normalization of 108 Caucasian male face images). Not only does the system 100 allow for the time course of individual face classification to be more reliable and thorough but, it also utilizes its outcomes for the purpose of facial feature derivation and image reconstruction.

Advantageously, EEG-based reconstruction, using the system 100, allows for the ability to clarify the dynamics of visual representations as they develop in response to a given stimulus. For instance, it can speak to how a percept evolves over time in response to a static stimulus by inspecting image reconstruction across consecutive time windows. In further embodiments, to the system 100 can also recover fine-grained dynamic information as present in moving stimuli. The superior temporal resolution of EEG could make movie modalities an efficient choice for the recovery of dynamic visual information.

While the embodiments described herein generally use 12 channels, other channel quantities can be used. For example, to determine a minimum number of channels needed to maximize classification and reconstruction results, the present inventors conducted EEG feature selection across the data of multiple participants. In this case, since electrodes sometimes carry irrelevant or redundant information at multiple time points, eliminating this information from higher-dimensional spatiotemporal patterns (e.g., across all electrodes and time points) could benefit classification and reconstruction. One embodiment of this procedure involved a sequence of steps as follows: (i) recursive feature elimination (RFE) was conducted to rank the value of different subsets of EEG channels for classification purposes using the data of one group of participants (i.e., training group); (ii) estimates of classification accuracy were computed for different subsets of EEG channels to identify the channel subset that maximizes accuracy using the data of another group of participants (i.e., validation group); (iii) an independent estimate of classification for the optimal subset of channels was computed in a third group of participants (i.e., test group). As an example, the minimum number of channels needed to achieve maximum classification and reconstruction of individual faces and words was estimated as 12 to 14 (out of 64). This quantity of channels has positive implications for data collection and analysis (i.e., by reducing memory and processing load), for usability purposes (i.e., by shortening set-up times and, thus, participant/user comfort), as well as for the potential design of dedicated hardware (i.e., by reducing costs associated with the use of a smaller number of channels).

Given the high temporal resolution of EEG recordings, the embodiments described herein can be used for frame-by-frame reconstructions of video stimuli (or of dynamic memory/imagery content). In a particular case, the present embodiments can be modified such that instead of using a single epoch, a sliding window can be applied to EEG recordings starting 50 ms after the onset of the visual process. The optimal length of this window can be determined through a procedure of feature selection, for example, using Recursive Feature Elimination (RFE). In this way, the reconstruction described herein can be applied to any position of the sliding window to deliver an approximation of the visual mental content captured by the respective window; for example, a sequence of words in a sentence or a face changing expressions.

While the current system and methods described herein generally focus on faces and words as a visual category of interest, the embodiments described herein can inform individual object recognition more generally, to any suitable visual categories or objects. It is noted that other visual similarity spaces are useable with the system 100 due to the presence of common neurocomputational principles underlying face and object identification as well as, methodologically, by the ability to evaluate the dynamics of invariant object recognition.

Although the foregoing has been described with reference to certain specific embodiments, various modifications thereto will be apparent to those skilled in the art without departing from the spirit and scope of the invention as outlined in the appended claims. The entire disclosures of all references recited above are incorporated herein by reference.

The invention claimed is:

1. A computer-implemented method for generating visual category reconstruction from electroencephalography (EEG) signals, the method comprising:
   receiving scalp EEG signals from one or more channels;
   using a trained pattern classifier, determining pairwise discrimination of the EEG signals, the pattern classifier trained using a training set comprising EEG signals associated with a subject experiencing different known visual identities;
   determining discriminability estimates of the pairwise discrimination of the EEG signals by constructing a confusability matrix;
   generating a multidimensional visual representational space;
   determining visual features for each dimension of the visual representational space by determining weighted sums of image stimulus properties;
   identifying subspaces determined to be relevant for reconstruction;
   reconstructing the visual appearance of a reconstruction target using estimated coordinates of the target and a summed linear combination of the visual features proportional with the coordinates of the target in the visual representational space; and
   outputting the reconstruction.

2. The method of claim 1, further comprising separating the EEG signals into epochs by selecting recordings from a given temporal interval relative to a specific event.

3. The method of claim 2, wherein the EEG signals from multiple epochs pertaining to the same specific event are averaged.

4. The method of claim 1, wherein the pattern classifier comprises a linear Support Vector Machine.

5. The method of claim 4, further comprising determining classification accuracy for each pair of the pairwise discrimination by averaging across iterations.

6. The method of claim 1, wherein generating the multidimensional visual representational space comprises estimating a fit between homologous spaces by aligning one space to the other and measuring the badness of fit as the sum of squared errors (SSE) between the two spaces.

7. The method of claim 1, wherein identifying the subspaces comprises determining dimensions containing pixel values significantly different from chance.

8. The method of claim 1, wherein the visual features are from human facial images, and wherein determining the visual features comprises:
   converting face stimuli to a CIEL*a*b* color space;
   summing the face stimuli proportionally to their normalized coordinates on a given dimension of face space; and
   determining the visual features as a linear approximation of the summed face stimuli along a specific dimension.

9. The method of claim 8, wherein reconstructing the visual appearance of the reconstruction target comprises aligning at least one expressive face space to a neutral face space using Procrustes transformation, and projecting a remaining expressive face space into the neutral face space using parameters of a Procrustes mapping function.

10. The method of claim 1, wherein the visual features are images of words, and wherein determining the visual features comprises:
    summing word stimuli proportionally to their normalized coordinates on a given dimension of visual word space; and
    determining the visual features as a linear approximation of the summed word stimuli along a specific dimension.

11. The method of claim 10, wherein reconstructing the visual appearance of the reconstruction target comprises aligning at least an uppercase visual word space to a lowercase visual word space counterpart using Procrustes transformation, and projecting a remaining uppercase visual word space into the lowercase visual word space using parameters of a Procrustes mapping function.

12. The method of claim 1, wherein the EEG signals are collected from twelve electrodes situated over homologue occipitotemporal areas.

13. A system for generating visual category reconstruction from scalp electroencephalography (EEG) signals, the system comprising one or more processors and a data storage device, the one or more processors configured to execute:
    an input module to receive the scalp EEG signals from one or more channels;
    a classification module to, using a trained pattern classifier, determine pairwise discrimination of the EEG signals, the pattern classifier trained using a training set comprising EEG signals associated with a subject experiencing different known visual identities;
    a reconstruction module to:
       determine discriminability estimates of the pairwise discrimination of the EEG signals by constructing a confusability matrix;
       generate a multidimensional visual representational space;
       determine visual features for each dimension of the visual representational space by determining weighted sums of image stimulus properties;
       identify subspaces determined to be relevant for reconstruction; and reconstruct the visual appearance of a reconstruction target using estimated coordinates of the target and a summed linear combination of the visual features proportional with the coordinates of the target in the visual representational space; and a display module to output the reconstruction.

14. The system of claim 13, wherein the pattern classifier comprises a linear Support Vector Machine.

15. The system of claim 13, wherein generating the multidimensional visual representational space comprises estimating a fit between homologous spaces by aligning one space to the other and measuring the badness of fit as the sum of squared errors (SSE) between the two spaces.

16. The system of claim 13, wherein identifying the subspaces comprises determining dimensions containing pixel values significantly different from chance.

17. The system of claim 13, wherein the visual features are from human facial images, and wherein determining the visual features comprises:

converting face stimuli to a CIEL*a*b* color space;

summing the face stimuli proportionally to their normalized coordinates on a given dimension of face space; and determining the visual features as a linear approximation of the summed face stimuli along a specific dimension.

18. The system of claim 17, wherein reconstructing the visual appearance of the reconstruction target comprises aligning at least one expressive face space to a neutral face space using Procrustes transformation, and projecting a remaining expressive face space into the neutral face space using parameters of a Procrustes mapping function.

19. The system of claim 13, wherein the visual features are images of words, and wherein determining the visual features comprises:

summing a word stimuli proportionally to its normalized coordinates on a given dimension of visual word space; and determining the visual features as a linear approximation of the summed word stimuli along a specific dimension.

20. The system of claim 19, wherein reconstructing the visual appearance of the reconstruction target comprises aligning at least capital letter visual word space to a lowercase visual word space counterpart using Procrustes transformation, and projecting a remaining capital letter visual word space into the lowercase visual word space using parameters of a Procrustes mapping function.

* * * * *